(12) United States Patent
Ray, II

(10) Patent No.: US 11,173,163 B2
(45) Date of Patent: Nov. 16, 2021

(54) TOPICAL ANTIMICROBIAL COMPOSITIONS AND METHODS OF FORMULATING THE SAME

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 0 days.

(21) Appl. No.: 16/702,085

(22) Filed: Dec. 3, 2019

(65) Prior Publication Data

US 2020/0101082 A1 Apr. 2, 2020

Related U.S. Application Data

(63) Continuation-in-part of application No. 16/270,335, filed on Feb. 7, 2019, which is a continuation-in-part of application No. 15/976,579, filed on May 10, 2018, application No. 16/702,085, which is a continuation-in-part of application No. 15/881,009, filed on Jan. 26, 2018, said application No. 15/976,579 is a continuation-in-part of application No. 15/668,184, filed on Aug. 3, 2017, said application No. 15/881,009 is a continuation-in-part of application No. 15/625,989, filed on Jun. 16, 2017, now abandoned, said application No. 15/976,579 is a continuation-in-part of application No. 15/597,936, filed on May 17, 2017, now Pat. No. 10,105,342, said application No. 15/625,989 is a continuation-in-part of application No. 15/440,800, filed on Feb. 23, 2017, said application No. 15/597,936 is a continuation-in-part of application No. 15/440,800, said application No. 15/976,579 is a continuation-in-part of application No. 14/990,168, filed on Jan. 7, 2016, said application No. 15/625,989 is a continuation-in-part of application No. 14/975,172, filed on Dec. 18, 2015, now Pat. No. 9,707,229, said application No. 15/597,936 is a continuation-in-part of application No. 14/975,172, and a continuation-in-part of application No. 14/819,342, filed on Aug. 5, 2015.

(60) Provisional application No. 62/370,571, filed on Aug. 3, 2016, provisional application No. 62/298,994, filed on Feb. 23, 2016, provisional application No. 62/298,991, filed on Feb. 23, 2016.

(51) Int. Cl.
| | |
|---|---|
| A61K 31/545 | (2006.01) |
| A61K 9/00 | (2006.01) |
| A61K 31/415 | (2006.01) |
| A61K 31/546 | (2006.01) |
| A61K 9/08 | (2006.01) |
| A61K 31/4178 | (2006.01) |

(52) U.S. Cl.
CPC .......... *A61K 31/546* (2013.01); *A61K 9/0014* (2013.01); *A61K 9/0031* (2013.01); *A61K 9/0034* (2013.01); *A61K 9/0043* (2013.01); *A61K 9/0046* (2013.01); *A61K 9/0053* (2013.01); *A61K 9/0078* (2013.01); *A61K 9/08* (2013.01); *A61K 31/4178* (2013.01)

(58) Field of Classification Search
CPC ...... A61K 31/546; A61K 9/00; A61K 9/0031; A61K 9/0043; A61K 9/0046; A61K 9/0075; A61K 9/08; A61L 9/0014
USPC .......................... 424/400, 489, 46; 514/206
See application file for complete search history.

(56) References Cited

U.S. PATENT DOCUMENTS

| | | | | |
|---|---|---|---|---|
| 5,776,926 | A * | 7/1998 | Bolz | A61K 31/546 514/200 |
| 6,056,955 | A * | 5/2000 | Fischetti | A61K 38/47 424/443 |
| 2007/0212340 | A1* | 9/2007 | Fischetti | A61K 38/162 424/94.2 |
| 2010/0168233 | A1* | 7/2010 | Jayes | A61P 17/00 514/557 |

FOREIGN PATENT DOCUMENTS

WO WO-2007098868 A1 * 9/2007 ............. A61K 45/06

OTHER PUBLICATIONS

Chiriac Chloronychia: "Green nail syndrome caused by Pseudomonas aeruginosa in elderly persons," Clinical Interventions in Aging, Jan. 2015, vol. 10, pp. 265-267. (Year: 2015).*

* cited by examiner

*Primary Examiner* — Shengjun Wang
(74) *Attorney, Agent, or Firm* — Akerman LLP; Mark D. Passler

(57) ABSTRACT

A method of treating a bacterial infection of a subject includes topically administering a topical composition that includes cefixime combined with a carrier. The topical composition may be administered by contacting a tissue surface of the subject to be treated with the topical composition such as skin or mucosal tissue.

7 Claims, No Drawings

TOPICAL ANTIMICROBIAL COMPOSITIONS AND METHODS OF FORMULATING THE SAME

CROSS-REFERENCE TO RELATED APPLICATIONS

This patent application is a continuation in-part application of co-pending U.S. patent application Ser. No. 15/881,009, filed Jan. 26, 2018, and is also a continuation in-part application of co-pending U.S. patent application Ser. No. 16/270,335, filed Feb. 7, 2019, each of which is hereby incorporated by reference in its entirety. U.S. patent application Ser. No. 15/881,009 is a continuation in-part of U.S. patent application Ser. No. 15/625,989, filed Jun. 16, 2017, which is a continuation-in-part of U.S. patent application Ser. No. 14/975,172 (now U.S. Pat. No. 9,707,229), filed Dec. 18, 2015, and U.S. patent application Ser. No. 15/440,800, filed Feb. 23, 2017. U.S. patent application Ser. No. 16/270,335 is a continuation-in-part of U.S. patent application Ser. No. 15/976,579, filed May 10, 2018, which is a continuation-in-part of U.S. patent application Ser. No. 14/990,168, filed Jan. 7, 2016, U.S. patent application Ser. No. 15/597,936 (now U.S. Pat. No. 10,105,342), filed May 17, 2017, and U.S. patent application Ser. No. 15/668,184, filed Aug. 3, 2017. U.S. patent application Ser. No. 15/597,936 is a continuation-in-part application of U.S. patent application Ser. No. 15/440,800, filed Feb. 23, 2017, U.S. patent application Ser. No. 14/975,172, (now U.S. Pat. No. 9,707,229) filed Dec. 18, 2015, and U.S. patent application Ser. No. 14/819,342, filed Aug. 5, 2015. U.S. patent application Ser. No. 15/440,800 claims the benefit of U.S. Provisional Patent Application No. 62/298,991, filed Feb. 23, 2016, and U.S. Provisional Patent Application No. 62/289,994, filed Feb. 23, 2016. U.S. patent application Ser. No. 15/668,184 claims the benefit of U.S. Provisional Patent Application No. 62/370,571, filed on Aug. 3, 2016. Each of the provisional and nonprovisional patent applications listed above is hereby incorporated by reference in its entirety.

TECHNICAL FIELD

The present application relates to compounded compositions, methods of making compounded compositions, and methods of using compounded compositions to treat or prevent an infection. The present application also relates to antimicrobial agents and methods of using antimicrobial agents to treat or prevent an infection.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Foot infections can be difficult problems for physicians to treat because of the biomechanical complexities of the extremity and the underlying circumstances that cause the infections. Soft tissue infections in the foot consist of any infectious process affecting the skin, subcutaneous tissue, adipose tissue, superficial or deep fascia, ligaments, tendons, tendon sheaths, joints, and/or joint capsules. Considering that there are more than 20 joints, 44 tendons, approximately 100 ligaments, 4 major compartments, and numerous fascial planes in the normal foot, the potential for complex problems is high.

Bacterial infections of the feet can occur as collections of pus, such as an abscess following a puncture wound or an infected hair follicle. These types of infections are usually red and elevated, and sometimes can be mistaken for an insect bite. There are many types of bacteria that cause an abscess, but staph are a leading cause. Bacterial skin infections can also resemble a rash, appearing as a reddened, tender, and warm area of skin. This type of infection is called cellulitis and can spread quickly, leading to red streaks that move from the foot toward the leg. The appearance of streaks is known as lymphangitis, which means the infection is spreading toward the lymph nodes. Cellulitis and lymphangitis can be caused by a variety of types of bacteria, but staph and sometimes streptococcus are the most common causes. Any infection, especially cellulitis and lymphangitis, requires prompt medical attention to avoid further spreading and complications. If left untreated, then some infections can spread to deeper tissues, including bone.

Certain fungal infections of the skin known as tinea infections are caused by dermatophytes, which are members of the *Trichophyton, Microsporum,* and *Epidermophyton* species. These mold-like fungi thrive in warm, moist areas, thriving on the dead tissues of hair, nails, and outer skin layers. Tinea infections include tinea pedis, known as athlete's foot; tinea corporis, known as ringworm; tinea capitis, a fungal infection of the scalp that can cause hair loss; tinea cruris, known as jock itch or tinea of the groin; tinea unguum, which is tinea of the nails; and tinea versicolor, a superficial fungal infection that produces brown, tan, or white spots on the trunk of the body. Tinea infections are contagious and can be passed through direct contact or by contact with clothing, from shower and pool surfaces, and even from pets.

Athlete's foot or tinea pedis is by far the most common form, with more than 12 million people in the United States suffering from the disease per year. It presents with redness, itching, burning, cracking, scaling, swelling, and occasionally bleeding. Athlete's foot includes toe web infections, moccasin type infections, and vesicular type infections. The condition generally includes small vesicles, fissures, scaling, maceration, hyper keratinization, and eroded areas between the toes and on the plantar surface of the foot, as well as on other skin areas. For example, the nails may show thickening, pitting, and subungual debris.

Reoccurrences of the infection are frequent. For some subjects, such as those also diagnosed with diabetes or circulatory problems, or obese subjects, tinea infections and their treatment can be quite serious. The source of the affliction often is a public safety and health concern, as the occurrence of tinea pedis is higher in public areas such as locker rooms, public showers, sports facilities, and the like.

Moreover, there are at least three different types of nail infections caused by fungi. The most common infection is frequently caused by Trichophyton rubrum and affects the nail bed and the area beneath the nail. Another type of infection affects only the nail surface and creates white or light colored patches. This second type of fungal infection is unusual and represents only about 10% of the reported cases. A third type of fungal infection affects the nail root and usually afflicts persons with impaired immune defense. A fourth (and unusual) type is caused by an infection of yeast fungi. Infections by yeast most often only affect nails that already are infected or damaged in some way.

Fungi are invasive to keratin nail tissue. Apart from becoming discolored and brittle, the nail may often separate from the nail bed. In addition, pain and difficulty in wearing foot apparel is often experienced. Initially, the disease affects only one nail, typically one nail of the foot, and is thereafter spread to more nails. The palms of the hands and the soles of the feet may frequently be affected as well. When the skin is affected, red spots frequently occur and the skin may peel off. Nail fungal infections are one of the hardest forms of external infection to treat, of which infections of toe nails are the most difficult to treat.

Wound healing is another area impacted by microbial organisms. Wound healing is a complex and dynamic process in which tissues repair from damage. The process generally includes a hemostasis phase, an inflammation phase, a granulation tissue formation phase, and a tissue remodeling phase. Wounds may occur from broken or unbroken skin as a result of blunt trauma, punctures, excessive exposure to cold or heat, chemical exposure, radiation exposure, and surgical procedures. Wounds may also arise as itching, scaling, swelling, or blistering of the skin. Wounds may also arise from eczemas, chronic skin conditions such as psoriasis, rosacea, and conditions accompanying bacterial, viral, or fungal infections may also damage skin.

Many factors can complicate or interfere with normal adequate wound healing. For example, such factors include age, infection, poor nutrition, immunosuppression, medications, radiation, diabetes, peripheral vascular disease, systemic illness, smoking, or stress. Abnormal wound healing can increase susceptibility to local infection, which also increases the risk systemic infection. What is needed are additional and alternative wound healing compositions for the treatment of wounds.

Despite advances in the understanding of the pathology of bacterial infections and fungal infections, there is still a need for compositions and methods that efficiently treat or prevent the progression and reoccurrence of bacterial infections and/or fungal infections that affect at least part of one or both feet.

SUMMARY

In one aspect, a method of treating a bacterial infection of a subject includes topically administering a topical composition that includes cefixime combined with a carrier. The topical composition may be administered by contacting a tissue surface of the subject to be treated with the topical composition such as skin or mucosal tissue.

In various embodiments, the topical composition may be administered in a dosage amount of between approximately 200 mg and approximately 400 mg cefixime. The topical composition may be topically administered once or twice daily. In one example, the topical composition may be topically administered twice daily and the topical composition comprises approximately 400 mg cefixime in each topical administration.

In some embodiments, the carrier comprises an aqueous solution and the topical composition comprises a solution format. In one example, the tissue surface comprises an ear of the subject and administering the topical composition comprises administering the solution to an ear canal in one or more drops. In another example, the tissue surface comprises a lung of the subject and administering the topical composition comprises nebulizing the solution for inhalation by the subject to deliver the topical composition to an infected mucosal tissue of the lung. In yet another example, the tissue surface comprises a nasal cavity of the subject and administering the topical composition comprises contacting infected mucosal tissue of the nasal cavity via irrigation, spray, or nasal nebulization. In still yet another example, the tissue surface comprises a vagina or anus of the subject and administering the topical composition comprises contacting infected mucosal tissue of the vagina or anus with the solution. In another example, the tissue surface comprises a mouth of the subject and administering the topical composition comprises contacting infected mucosal tissue of the mouth with the solution. In yet another example, the infected surface comprises skin of the subject, and wherein administering the topical composition comprises spraying the solution onto the infected skin surface, irrigating the infected skin surface with the solution, or submerging the infected skin surface in the solution.

In some embodiments, the carrier comprises an ointment, cream, gel, or lotion and the topical composition is formulated in an ointment, cream, gel, or lotion format. In one example, the tissue surface comprises a vagina or anus of the subject and administering the topical composition comprises applying the ointment, cream, gel, or lotion onto the infected mucosal tissue of the vagina or anus. In another example, the tissue surface comprises a mouth of the subject and administering the topical composition comprises applying the ointment, cream, gel, or lotion onto infected mucosal tissue of the mouth. In still another example, the tissue surface comprises skin of the subject and administering the topical composition comprises applying the ointment, cream, gel, or lotion onto the infected skin surface.

In some embodiments, the carrier comprises a powder and the topical composition comprises a powder format. In one example, the tissue surface comprises mucosal tissue and administering the topical composition comprises applying the powder onto the infected mucosal tissue. In another example, the infected mucosal tissue is mucosal tissue of the lungs, nasal cavity, mouth, vagina, or anus. In still another example, the tissue surface comprises skin of the subject and administering the topical composition comprises applying the powder onto the infected skin.

DESCRIPTION

The present disclosure describes compounded compositions for topical administration. A compounded composition according to the present disclosure may include a topical composition formulated for topical administration to an external surface of a mammal, such as a human. In some embodiments, the topical composition may be formulated to treat infections or suspected infections of tissues and may be topically administered to surface tissues comprising or adjacent tissues thereof, which may include nails, wounded tissue, mucosal surfaces of the vagina or anus, skin such as on hands, feet, scalp, torso, arms, legs, or other surface. Embodiments of the composition may also be formulated to be applied to nails, a vaginal orifice, or anal orifice. Embodiments of the composition may be formulated for topical application tissues of a nose, mouth, e.g., mouth rinse, wash, or gargle, lung, or ear. Such a composition may be referred to herein as a topical composition.

The topical composition may generally include an antimicrobial agent comprising one or more pharmaceuticals drugs. Some embodiments may include combinations of active agents described herein without the antimicrobial agent. The topical composition may include a carrier comprising one or more carrier components. Unless stated otherwise, carrier is intended to include carrier component such that use of the term carrier may refer to a component of the carrier and is not restrictive in that other carrier components may be included and the carrier component referred to as the carrier need not form a complete carrier. Indeed, a carrier may include a thickening agent added to a commercially available medicated carrier solution, lotion, or cream, alone or together with other carriers, to formulate a carrier with respect to the topical composition. Carrier may also be used interchangeably with the term base. Carrier may refer to a diluent and/or medium within which active agents are dissolved, suspended, or dispersed. The carrier may be liquid, semiliquid, or solid. For example, the carrier may include an aqueous, organic, or inorganic solution, which may include a suspension/dispersion, cream, gel, ointment, lotion, emulsion, powder, or paste. The topical composition may be formulated to treat microbial infections, such as infections of the skin, nails, mucosal surfaces (such as mucosal surfaces of vulva, vagina, anus, nose, mouth, ear, pharynx, upper respiratory tract, lungs), and potentially internalized infections, e.g., via transdermal administration of antimicrobial agents.

Embodiments of the topical composition may include an antimicrobial agent selected from an antibacterial component, antifungal component, or both. In one embodiment, the antibacterial component may include an antiviral component comprising one or more antiviral pharmaceutical drugs. As introduced above, the topical composition may comprise the antimicrobial agent alone or in combination with one or more additional active agents selected from an anti-inflammatory agent, steroid agent, anti-allergic agent, anti-depressant agent, stimulant agent, disinfectant agent, mucolytic agent, anticonvulsant agent, local anesthetic agent, or combinations thereof. In one embodiment, the topical composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In some embodiments, the topical composition may comprise the antimicrobial agent including an antifungal component, antibacterial component, or both alone or in combination with a steroid agent, antiviral agent, NSAID agent, antidepressant agent, anticonvulsant agent, analgesic agent, opiate or opioid agonist agent, keratolytic agent, or combination thereof.

It is to be appreciated that recitations herein of active pharmaceuticals include pharmaceutical equivalents such as pharmaceutically acceptable salts thereof whether or not specifically recited as such. Similarly, recitation of a particular active pharmaceutical salt may also include other pharmaceutically acceptable salts thereof whether or not specifically recited as such.

In various embodiments, the antimicrobial agent comprises an antifungal component, alone or in combination with an antibacterial component, wherein the an antifungal component includes one or more antifungal pharmaceutical drugs selected from one or more categories of antifungal components including azoles (imidazoles), antimetabolites, allylamines, morpholine, glucan synthesis inhibitors (echinocandins), polyenes, benoxaaborale; other antifungal/onychomycosis agents, and new classes of antifungal/onychomycosis agents. For example, the antifungal component may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In some embodiments, the antibacterial component is selected from one or more azoles. In one example, the antifungal component is selected from itraconazole, voriconazole, or combination thereof. In various embodiments, the antimicrobial agent comprises an antifungal component selected from one or more antifungals comprising fluconazole, itraconazole, voriconazole, amphotericin, nystatin, clotrimazole, econazole, or ketoconazole.

In various embodiments, the topical composition may comprise between approximately 0.01% and approximately 20% by weight antifungal component, such as between approximately 0.01% and approximately 5%, approximately 0.01% and approximately 3%, approximately 0.01% and approximately 1%, approximately 0.01% and approximately 0.25%, approximately 0.01% and approximately 0.15%, approximately 0.05% and approximately 0.15%, between 0.1% and 10%, approximately 0.1% and approximately 0.5%, approximately 0.1% and approximately 0.2%, approximately 0.2% and approximately 0.8%, approximately 0.2% and approximately 0.6%, approximately 0.2% and approximately 0.4%, approximately 0.3% and approximately 1%, approximately 0.3% and approximately 0.8%, approximately 0.3% and approximately 0.6%, approximately 0.4% and approximately 1%, approximately 0.5% and approximately 1%, approximately 0.5% and approximately 8%, approximately 0.6% and approximately 1%, approximately 0.6% and approximately 0.8%, approximately 0.8% and approximately 1%, approximately 1% and approximately 3%, approximately 1% and approximately 10%, approximately 1% and approximately 8%, approximately 1% and approximately 5%, approximately 1% and approximately 3%, approximately 3% and approximately 10%, approximately 3% and approximately 8%, approximately 3% and approximately 5%, between 5% and 10%, approximately 5% and approximately 8%, approximately 6% and approximately 10%, approximately 6% and approximately 8%, approximately 7% and approximately 10%, approximately 8% and approximately 10%, approximately 10% and approximately 20%, approximately 10% and approximately 15%, approximately 10% and approximately 12%, approximately 12% and approximately 15%, or between approximately 15% and approximately 20% antifungal component by weight. In some embodiments, the amount of antifungal component by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical composition.

In various embodiments, the topical composition comprises an antimicrobial agent including an antifungal component alone or in combination with an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a local anesthetic agent, or combination thereof, which may include one or more active pharmaceutical drugs of selected agents or components thereof. In one embodiment, the topical composition includes one or more additional active agents selected from one or more anticonvulsants, nerve depressants, muscle relaxants, NMDA (N-Methyl-D-aspartate) receptor antagonists, opiate or opioid agonists, antidepressants, and/or other actives. In some embodiments, the topical composition comprises an antifungal component alone or in combination with an antibacterial component, antiviral component, steroid agent, NSAID agent, antidepressant agent, anticonvulsant agent, mucolytic agent, analgesic agent, opioid agent, keratolytic agent, or combination thereof, which may include one or more active pharmaceutical drugs of selected components or agents. In an above or another embodiment, the antimicrobial agent may further comprise an antibacterial component comprising one or more antibacterial pharmaceutical drugs, such as those identified herein.

The antimicrobial agent may comprise an antibacterial component alone or in combination with an antifungal component. In some embodiments, the antibacterial component comprises one or more enicillins, cephalosporins, fluoroquinolones, aminoglycosides, monobactams, carbapenems, macrolides, other antibacterial, or combination thereof. For example, the antibacterial component may include one or more antibacterial pharmaceutical drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, methicillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilamide, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the antibacterial component is selected from mupirocin, gentamycin, tobramycin, or combinations thereof. In one embodiment, the antibacterial component includes an aminoglycoside.

In various embodiments, the antimicrobial agent comprises an antibacterial component selected from one or more antibacterial drugs comprising vancomycin, ciprofloxacin, levofloxacin, azithromycin, clindamycin, mupirocin, doxycycline, mupirocin, ceftriaxone, colistimethate, tobramycin, cefepime, gentamicin, streptomycin, sulfamethoxazole/trimethoprim. In one example, the topical composition comprises linezolid, levofloxacin, ciprofloxacin, or combination thereof. In an embodiment, the antimicrobial agent comprises cefixime, nitrofurantoin, tetracycline, or combination thereof.

In various embodiments, the topical composition may comprise between approximately 0.01% and approximately 20% by weight antibacterial component, such as between approximately 0.01% and approximately 5%, approximately 0.01% and approximately 3%, approximately 0.01% and approximately 1%, approximately 0.01% and approximately 0.25%, approximately 0.01% and approximately 0.15%, approximately 0.05% and approximately 0.15%, between 0.1% and 10%, approximately 0.1% and approximately 0.5%, approximately 0.1% and approximately 0.2% approximately 0.2% and approximately 0.8%, approximately 0.2% and approximately 0.6%, approximately 0.2% and approximately 0.4%, approximately 0.3% and approximately 1%, approximately 0.3% and approximately 0.8%, approximately 0.3% and approximately 0.6%, approximately 0.4% and approximately 1%, approximately 0.5% and approximately 1%, approximately 0.5% and approximately 8%, approximately 0.6% and approximately 1%, approximately 0.6% and approximately 0.8%, approximately 0.8% and approximately 1%, approximately 1% and approximately 3%, approximately 1% and approximately 10%, approximately 1% and approximately 8%, approximately 1% and approximately 5%, approximately 1% and approximately 3%, approximately 3% and approximately 10%, approximately 3% and approximately 8%, approximately 3% and approximately 5%, between 5% and 10%, approximately 5% and approximately 8%, approximately 6% and approximately 10%, approximately 6% and approximately 8%, approximately 7% and approximately 10%, approximately 8% and approximately 10%, approximately 10% and approximately 20%, approximately 10% and approximately 15%, approximately 10% and approximately 12%, approximately 12% and approximately 15%, or between approximately 15% and approximately 20% antibacterial component by weight. In some embodiments, the amount of antibacterial component by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical composition.

In various embodiments, the topical composition comprises an antimicrobial agent comprising an antifungal component comprising at least two antifungal pharmaceutical drugs, an antibacterial component comprising at least two antibacterial pharmaceutical drugs, or an antifungal component comprising one or more antifungal pharmaceutical drugs and an antibacterial component comprising one or more antibacterial pharmaceutical drugs.

In one example, the topical composition comprises one or more of mupirocin, azithromycin, cefixime, nitrofurantoin, or tetracycline and an antifungal component selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. The antifungal component may comprise itraconazole and/or fluconazole, for example. In one embodiment, the topical composition comprises mupirocin and itraconazole, mupirocin and nystatin, cefixime and itraconazole or fluconazole, nitrofurantoin and itraconazole or fluconazole, nitrofurantoin and tetracycline and one or both of itraconazole or fluconazole, or azithromycin and fluconazole. In another example, the topical composition comprises mupirocin and/or azithromycin and an additional antibacterial pharmaceutical drug identified herein.

In another example, the topical composition comprises an antifungal component including amphotericin b, ciclopirox, clotrimazole, econazole, fenticonazole, fluconazole, isoconazole, itraconazole, ketoconazole, naftifine, omoconazole, oxiconazole, polygodial, posaconazole, terbinafine, terconazole, tioconazole, tolnaftate, voriconazole, or combination thereof and a second, different, antimicrobial pharmaceutical drug. For example, the topical composition may comprise an antibacterial component comprising the second antimicrobial pharmaceutical drug that includes one or more antibacterial pharmaceutical drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In another example, the topical composition comprises an antifungal component including itraconazole and a second, different, antimicrobial pharmaceutical drug, comprising an additional antifungal pharmaceutical drug selected from an azole. In one example, the azole includes clotrimazole, econazole, fluconazole, isoconazole, ketoconazole, voriconazole, or combination thereof. In another example, the additional antifungal pharmaceutical drug is selected from antimetabolites, allylamines, morpholine, glucan synthesis inhibitors (echinocandins), polyenes, benoxaaborale; other antifungal/onychomycosis agents, and new classes of antifungal/onychomycosis agents. In another example, the additional antifungal pharmaceutical drug is selected from abafungin, albaconazole, amorolfin, anidulafungin, bifonazole, butenafine, butoconazole, candicidin, caspofungin, ciclopirox, fenticonazole, filipin, flucytosine, griseofulvin, haloprogin, hamycin, isavuconazole, micafungin, miconazole, naftifine, natamycin, omoconazole, oxiconazole, polygodial, posaconazole, ravuconazole, rimocidin, sertaconazole, sulconazole, terbinafine, terconazole, tioconazole, undecylenic acid, or a combination thereof. In another example, the additional antifungal pharmaceutical drug is selected from amphotericin b, nystatin, tolnaftate, or combination thereof.

In some examples, a topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, from approximately 3.0% w/w to approximately 7.0% w/w, or from approximately 4.0% w/w to approximately 7.0% w/w of an antifungal component identified herein. For example, the topical composition may comprise itraconazole, voriconazole, fluconazole, or combination thereof. In an example, the topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, from approximately 3.0% w/w to approximately 7.0% w/w, or from approximately 4.0% w/w to approximately 7.0% w/w of a first antifungal drug identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a second antifungal drug identified herein.

In various embodiments, the antimicrobial agent comprises an antibacterial agent selected from one or more antibacterials comprising doxycycline, ceftriaxone, cefixime, colistimethate, tobramycin, cefepime, gentamicin, streptomycin, sulfamethoxazole/trimethoprim, tetracycline, or nitrofurantoin. The topical composition may include a two or more antibacterial drugs. For example, in some embodiments, the topical composition comprises cefixime and an additional antibacterial pharmaceutical drug identified herein. In another example, the topical composition comprises tetracycline and/or nitrofurantoin and an additional antibacterial pharmaceutical drug identified herein.

In one example, the topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antibacterial component identified herein. In another example, the topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a first antibacterial drug identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a second antibacterial drug identified herein. For example, the topical composition may comprise mupirocin and tobramycin, mupirocin and doxycycline, mupirocin and doxycycline hyclate, mupirocin and azithromycin, or mupirocin, doxycycline, and ketoconazole, nitrofurantoin and tetracycline, or cefixime and mupirocin or doxycycline.

In one example, a topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antifungal component identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antibacterial component identified herein. For example, the antibacterial component may comprise nitrofurantoin, tetracycline, cefixime, doxycycline, tobramycin, ciprofloxacin, mupirocin, or combination thereof and the antifungal component may comprise ketoconazole, itraconazole, voriconazole, or combination thereof.

In some embodiments, the topical composition may comprise one or more excipients or additives. In an aspect, excipients or additives include, but are not limited to, the following: solvents, surfactants, humectants, preservatives, flavorings, stabilizers (including antioxidants), binders, and colorants.

In various embodiments, the topical composition comprises the antibacterial component alone or in combination with one or more additional active agents selected from an antifungal component, an antiviral agent, an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a mucolytic agent, a local anesthetic agent, or combinations thereof, which may include one or more active pharmaceutical drugs of selected agents. In one embodiment, the topical composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In some embodiments, the topical composition may comprise the antibacterial component alone or in combination with an antifungal component, steroid agent, antiviral component, NSAID agent, antidepressant agent, anticonvulsant agent, analgesic agent, opioid agent, keratolytic agent, or combination thereof, which may include one or more active pharmaceutical drugs of selected components or agents. In various embodiments, the topical composition may comprise the antibacterial component alone or in combination with one or more antifungal components.

As introduced above, the topical composition may comprise one or more additional active agents. It will be appreciated that topical compositions herein may include or specifically exclude additional active agents. It will also be appreciated that topical compositions may exclude an antimicrobial agent and rather include one or more of the additional active agents described herein.

In various embodiments, the topical composition comprises the antimicrobial agent and a nonsteroidal anti-inflammatory drug (NSAID) agent. The NSAID agent may include one or more NSAIDS selected from oxicams, such as meloxicam or piroxicam; salicylic acid derivatives, such as aspirin, diflunisal, salsalate, or trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, or tolmetin; fenamates, such as meclofenamate; and/or COX-2 inhibitors, such as celecoxib, rofecoxib, or valdecoxib. In various embodiments, the topical composition comprises between approximately 0.01% and approximately 20% by weight NSAID agent. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for nasal irrigation, nebulization to the upper or lower respiratory tract, ear, bath, spray, gauze, or irrigation of a foot, limb, torso, or wound, nail lacquer, mouth gargle, or mouth wash. The topical composition may be formulated into a cream, lotion, ointment, gel, shampoo, or lozenge for topical application to skin or mucosal tissue as described herein.

In some embodiments, the topical composition comprises the antimicrobial agent and a local anesthetic agent. The local anesthetic agent may be selected from lidocaine, prilocaine, benzocaine, or combination thereof. The local anesthetic agent may comprise between approximately 0.01% and approximately 15% by weight of the topical composition. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for nasal irrigation, nebulization to the upper or lower respiratory tract, ear, bath, spray, gauze, or irrigation of a foot, limb, torso, or wound, nail lacquer, mouth gargle, or mouth wash. The topical composition may be formulated as cream, lotion, ointment, gel, shampoo, or lozenge for topical application to skin or mucosal tissue as described herein.

In an embodiment, the topical composition comprises the antimicrobial agent a steroid agent. In one example, the steroid agent comprises a corticosteroid selected from amcinonide, betamethasone dipropionate, betamethasone valerate, clobetasol propionate, desoximetasone, diflorasone diacetate, flurandrenolide, fluticasone propionate, fluocinonide, halcinonide, halobetasol propionate, mometasone furoate, triamcinolone acetonide, or combination thereof. In various embodiments, the topical composition comprises between approximately 0.001% and approximately 1% by weight steroid agent. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for nasal irrigation, nebulization to the upper or lower respiratory tract, ear, bath, spray, gauze, or irrigation of a foot, limb, torso, or wound, nail lacquer, mouth gargle, or mouth wash. The topical composition may be formulated into a cream, lotion, ointment, gel, shampoo, or lozenge for topical application to skin or mucosal tissue as described herein.

In various embodiments, the topical composition comprises the antimicrobial agent and a muscle relaxant agent comprising one or more muscle relaxants selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants. In various embodiments, the topical composition comprises between approximately 0.001% and approximately 5% by weight muscle relaxant agent. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for nasal irrigation, nebulization to the upper or lower respiratory tract, ear, bath, spray, gauze, or irrigation of a foot, limb, torso, or wound, nail lacquer, mouth gargle, or mouth wash. The topical composition may be formulated into a cream, lotion, ointment, gel, shampoo, or lozenge for topical application to skin or mucosal tissue as described herein.

In some embodiments, the topical composition comprises the antimicrobial agent and an anticonvulsant or nerve depressant agent. The anticonvulsant or nerve depressant agent may comprise one or more nerve depressants and/or anticonvulsants selected from gabapentin, topiramate, lamotrigine, or combinations thereof. In various embodiments, the anticonvulsant or nerve depressant agent may comprise between approximately 0.01% and approximately 20% by weight of the topical composition. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for nasal irrigation, nebulization to the upper or lower respiratory tract, ear, bath, spray, gauze, or irrigation of a foot, limb, torso, or wound, nail lacquer, mouth gargle, or mouth wash. The topical composition may be formulated into a cream, lotion, ointment, gel, shampoo, or lozenge for topical application to skin or mucosal tissue as described herein.

In one embodiment, the topical composition comprises the antimicrobial agent and a NMDA receptor antagonist agent such as ketamine. In some embodiments, the topical composition may comprise an opiate or opioid agonist agent selected from tramadol; one or more C2 opiate agonists selected from oxycodone, morphine, methadone, hydromorphone, and fentanyl; one or more C3 opiate agonists selected from hydrocodone, codeine, propoxyphene, butalbital, and pentazocine; or any combination thereof. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for nasal irrigation, nebulization to the upper or lower respiratory tract, ear, bath, spray, gauze, or irrigation of a foot, limb, torso, or wound, nail lacquer, mouth gargle, or mouth wash. The topical composition may be formulated into a cream, lotion, ointment, gel, shampoo, or lozenge for topical application to skin or mucosal tissue as described herein.

In an embodiment, the topical composition comprises the antimicrobial agent a keratolytic agent selected form urea, salicylic acid, papain, or combinations thereof. For example, the topical composition may comprise the antimicrobial agent and urea. In various embodiments, the topical composition may comprise between approximately 1% and approximately 30% by weight urea. In an embodiment, the antimicrobial agent comprises cefixime, nitrofurantoin, tetracycline, or combination thereof. Additional antimicrobial agents may also be included. The topical composition may be formulated as a solution, which may include a suspension/dispersion, for irrigation of a foot, limb, torso, or wound, or nail lacquer. The topical composition may be formulated into a cream, lotion, ointment, gel, or shampoo for topical application to skin or mucosal tissue as described herein.

In an embodiment, the topical composition comprises an antibacterial component comprising cefixime, tetracycline, nitrofurantoin, or combinations thereof alone or in combination with one or more additional active agents selected from an antifungal component, an antiviral agent, an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a mucolytic agent, a local anesthetic agent, or combinations thereof, which may include one or more active pharmaceutical drugs of selected agents. In one example, the topical composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In one example, the topical composition may comprise the antibacterial component alone or in combination with an antifungal component, steroid agent, antiviral component, NSAID agent, antidepressant agent, anticonvulsant agent, analgesic agent, opioid agent, keratolytic agent, or combination thereof, which may include one or more active pharmaceutical drugs of selected components or agents. In various embodiments, the topical composition may comprise the antibacterial component alone or in combination with one or more antifungal components identified herein.

The topical composition may be provided in a topical format, which may include a carrier for topical administration. In various embodiments, the topical composition may include a colloid or emulsion (o/w, w/o), cream, lotion, ointment, foam, aqueous or non-aqueous gel, aqueous or non-aqueous solution, which may include a suspension/dispersion, powder, nail lacquer, bath, or paste. The topical composition, for example, may comprise an antibacterial component comprising cefixime, tetracycline, nitrofurantoin, or combinations thereof alone or in combination with one or more additional active agents provided in an above topical format.

The topical composition may be administered topically by contacting an external surface of the body, which may include skin, e.g., intact, wounded, broken skin; nails; mucosal tissue lining a vaginal or anal orifice. The topical composition may be administered topical by contacting mucosal surfaces of vulva, vagina, anus, nose, mouth, ear, pharynx, upper respiratory tract, or lungs. The topical composition may be administered in a spray, coating, soak, powder, spread, lozenge, chewable, rinse, or the like, for example, suitable to the topical format. The topical composition, for example, may comprise an antibacterial component comprising cefixime, tetracycline, nitrofurantoin, or combinations thereof alone or in combination with one or more additional active agents provided in an above topical format.

The topical composition may comprise a solution, which may comprise a suspension/dispersion; cream; an oil; a gel; an ointment; a lozenge; or a gum as also described herein. The topical composition, for example, may comprise an antibacterial component comprising cefixime, tetracycline, nitrofurantoin, or combinations thereof alone or in combination with one or more additional active agents provided in an above dosage form. Such dosage forms including the microbial agent may be delivered, for example, by application, dissolution, or irrigation at a body cavity or orifice or topically to skin or a mucosal surface, e.g., drops applied to tear ducts or a mouth rinse, wash, or gargle composition. In one example, the topical composition may be topically administered to infected skin forming the outer body covering of a subject or to mucosal tissue of the vagina, oral cavity, respiratory tract, lungs, ear canal, or anus to treat a microbial infection. For example, the topical composition may comprise a solution or suspension/dispersion for topical administration in an ear, hand, foot, mouth using a bath or irrigation. In another example, the topical composition comprises a nail lacquer for administration to nails. In some embodiments, the topical composition may be utilized as a wound treatment and administered to broken or unbroken skin or mucosal tissue as indicated above and elsewhere herein.

In various embodiments, the topical composition may comprise antimicrobial agent and/or antifungal agent as disclosed herein in a solution for nasal irrigation, e.g., via Neil-Med® Irrigation Delivery; medium particle size nasal delivery, e.g., via NasoNeb® Nasal Nebulizer; small particle size nasal delivery, e.g., via PARI SinuStar™; small particle size lung (respiratory) delivery, e.g., via Omron® or PARI nebulizers; ear delivery; topical bath irrigation; topical spray application; topical irrigation application; topical gauze application; or other topical external application. The topical composition, for example, may comprise an antibacterial component comprising cefixime, tetracycline, nitrofurantoin, or combinations thereof alone or in combination with one or more additional active agents provided in an above topical format for topical delivery to lungs, nasal cavity, throat, upper or lower respiratory tract, ear, skin, mucosal tissue, limbs, torso, or body orifice.

In various embodiments, the topical composition is formulated for suppository administration at a body orifice, such as the rectum, vagina, or urethra. In some embodiments, the composition may comprise a dosage form including a capsule, tablet, gum, lozenge, or pouch configured for sublingual or sub-labial administration. The body cavities or orifices may comprise one or more of the nasal cavity, nostrils, tear duct, anus, vagina, urethra, mouth, and ear canal.

The topical composition may be provided in an oral rinse solution or oral lozenge. The oral rinse may comprise a mouthwash. Oral administration may also include application or an ointment, lotion, cream, or gel.

In some embodiments, the topical composition comprises a nail lacquer for direct application to nail tissue. A nail lacquer format may include one or more antimicrobial actives formulated for topical application to nail tissue. In some embodiments, a nail lacquer format may include additives such as thickening agents, plasticizers, polymers, volatile organic compounds, or other additives to promote effective localization of the medication following application. In some embodiments, a nail lacquer format may comprise a solution. Solution is intended to encompass solvent and solute combinations wherein the solute is dissolved, suspended, dispersed, and/or mixed in the solute unless stated otherwise. In some embodiments, a nail lacquer format may lack traditional lacquer additives. In various embodiments, a nail lacquer format may comprise an aqueous solution formulated for application to a nail surface whereon the carrier evaporates or is absorbed. In some embodiments, a nail lacquer solution may have a fluid or semi-fluid consistency. In some embodiments, a carrier for a nail lacquer format may be thickened with a viscosity agent to increase viscosity for administration. In some embodiments, a nail lacquer format may comprise a solution comprising a cream, lotion, gel, or ointment.

Further to the above, in some embodiments, the topical composition comprises a treatment solution for a footbath, irrigation, or spray administration. In one example, the topical composition comprises a treatment solution for nasal or intranasal administration via irrigation or nebulization. In one example, the topical composition comprises a treatment solution for administration to an ear in a spray or drop. In one example, the topical composition comprises a treatment solution for administration to a mouth and comprises a drop, spit-rinse, mouthwash, or gargle format. In some embodiments, the topical composition may be administered to the mouth and comprises a lozenge, chewable, ointment, cream, lotion, or gel format.

Methods of Making a Topical Composition

In various embodiments, a method of formulating the topical composition comprises combining the active agents including the antimicrobial agent and a topical carrier. For example, the method may include combining an antifungal and/or antibacterial component and a carrier. In one example, the antimicrobial agent comprises an antibacterial component comprising cefixime, tetracycline, nitrofurantoin, or combinations thereof alone or in combination with one or more additional active agents described herein. Cefixime may be combined with a carrier and additional actives, if present, in an amount between approximately 100 mg and approximately 500 mg per dosage volume. Nitrofurantoin may be combined with a carrier and additional actives, if present, in an amount between approximately 25 mg and approximately 300 mg, such approximately 200 mg or less.

The carrier may include one or more vehicles/carriers. The carrier may be liquid, semi-liquid, or solid. For example, the carrier may include an aqueous, organic, or inorganic solution, which may include a suspension/dispersion, cream, gel, ointment, lotion, emulsion, powder, or paste. In some embodiments, the carrier includes a carrier or vehicle composition such as a base cream, ointment, gel, lotion, foam, or solution. The carrier may include carriers such as lecithin, phospholipids, glycols, paraffin, fatty acids, carbopols/carbomers, alcohols, lanolin, for example.

In some embodiments, the carrier comprises an aqueous or non-aqueous solution. In some examples, a carrier comprising an aqueous solution may be combined with the antimicrobial agent to formulate a topical composition comprising an irrigation solution, bath (e.g., footbath, soak), nail lacquer, drops, or topical spray, e.g., aerosol or nebulized, for example. In an embodiment, the carrier may include an aqueous solution comprising a saline solution. For example, the topical composition may comprise a carrier comprising a sodium chloride solution, which may be a sterile solution, an alcohol, dilute sodium hypochlorite, hydrogen peroxide, Dakin's solution, water, e.g., purified water, water for irrigation, water for injection, or a sterile water. In one embodiment, a carrier comprises a sodium chloride 0.9% solution, which may be a sterile sodium chloride 0.9% solution. The carrier may comprise an alcohol. The carrier may be present in an amount sufficient to obtain the desired amount of active agents per unit weight or volume.

The topical composition may include a carrier component comprising a polyethylene glycol (PEG) carrier component. In other embodiments, the composition is PEG-free. In these or other embodiments, the composition may include a silicon or silicon variant carrier component. In some embodiments, the composition is silicon-free. An example topical composition may comprise a solution including carrier components selected from water, alcohol, DMSO, saline or sodium chloride, hydrogen peroxide, sodium hypochlorite, or other aqueous or non-aqueous carrier medium into which the one or more active agents are mixed, suspended, dispersed, solubilized, or dissolved. The topical composition may be water soluble/miscible or formulated for water absorption. The topical composition may comprise a water-in-oil emulsion or oil-in-water emulsion. In one embodiment, the topical composition comprises an emulsion, e.g., a cream or lotion format, comprising one or more carrier components selected from of acrylate copolymer, alcohol, camphor, carbomer, dimethyl isosorbide, disodium EDTA, dl-alphatocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sodium hydroxide, sorbitol, stearic acid, zinc pyrithione, or combinations thereof. In some embodiments, the topical composition comprises a foam format that includes propellant carrier component such as butane. Topical compositions comprising a foam format may also comprise additional characteristics such as that of an emulsion, such as an oil-in-water emulsion, or gel.

In one example, the topical composition comprises an ointment format and includes active agents in a carrier comprising carrier components selected from hydrophilic petrolatum, white petrolatum, hydrophilic ointment, white ointment, anhydrous lanolin, hydrous lanolin, polyethylene glycol (PEG) ointment, or combinations thereof. In an embodiment, the topical composition comprises a gel format. The gel may be an aqueous or non-aqueous gel. The gel may include carrier components such as thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof. The topical composition may include a powder format and include carrier components such as lactose or talc, for example.

The topical composition or carrier thereof may include carrier components such as one or more solubilizers, stabilizers, buffers, tonicity modifiers, bulking agents, viscosity enhancers/reducers, surfactants, chelating agents, binders, humectants, preservatives, flavorings, colorants, adjuvants, or combinations thereof.

In various embodiments, the topical composition or carrier thereof comprises one or more glucose polymers such as a starch, cellulose, polydextrose, or combination thereof. Example starches may include sodium starch glycolate, corn starch, pregelatinized starch, or combination thereof. Example celluloses may include hydroxypropyl cellulose, hypromellose, croscarmellose sodium, ethyl cellulose, microcrystalline cellulose, or combination thereof. Povidone such as povidone K30, copovidone, crospovidone, or combination thereof, may also be present. In some embodiments, glycol and/or a sugar alcohol may be present. Example glycols may include polyethylene glycol, propylene glycol, or combination thereof. Example sugar alcohols may include mannitol. Some embodiments may include oxides such as silicon dioxide, titanium dioxide, ferric oxide, or combination thereof. One embodiment may include any of the above and magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof. In one embodiment, the topical composition does not include one or more of starch, cellulose, polydextrose, sodium starch glycolate, corn starch, pregelatinized starch, hydroxypropyl cellulose, hypermellose, croscarmellose sodium, ethyl cellulose, microcrystalline cellulose, povidone, povidone K30, copovidone, crospovidone, polyethylene glycol, propylene glycol, mannitol, silicon dioxide, titanium dioxide, ferric oxide, magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof.

As introduced above, the method may include combining the carrier and a powder containing all or a portion of the antimicrobial agent. For example, antifungal component comprising one or more antifungal actives and/or antibacterial component comprising one or more antibacterial actives may be obtained from bulk powder or powder for injection and combined with the carrier. In one of an above or another example, one or more actives of the antimicrobial agent may be obtained from one or more commercially available oral capsules or tablets. Oral capsules may be opened to release contained powder or solubilized for combination with the carrier. The oral tablets may be crushed and the resulting powder may be combined with the carrier.

In addition to antimicrobial active drug, in various embodiments, powder from a capsule or crushed antimicrobial tablet may include excipients. For example, antimicrobial tablets may include one or more of a glucose polymer, starch, and/or cellulose and one or more additional components such as magnesium stearate, povidone, lactose, glycol, oxide, talc, triacetin, or an alcohol. In some embodiments, the resulting powder includes a cellulose such as microcrystalline cellulose and one or more of magnesium stearate, anhydrous dibasic calcium phosphate, or povidone. In one example, the powder may further include croscarmellose sodium. In a further example, the powder may also include an oxide such as silicon dioxide, ferric oxide, aluminum oxide, or combination thereof; a starch, such as sodium starch glycolate, corn starch, or both; sodium lauryl sulfate, lactose, talc, or combinations thereof. In some embodiments, wherein the tablet includes a film coating, the method may include removal of all or a portion of a film coating.

When the method includes addition of crushed oral tablets, less than all the powder of a crushed tablet may be used when the tablet contains more active drug than required. More than one crushed tablet may be used when the method includes formulating a topical composition comprising more active drug than is present in a single tablet. Similarly, the method may include addition of less than all powder of a capsule or multiple capsules.

In an embodiment, powder obtained from a crushed antimicrobial drug tablet may be added to a carrier for compounding, such as a base for compounding, or a commercially available medicated composition.

Tablets may include film coatings. For example, film coatings may comprise polymer coatings such as a shellac. In some embodiments, the method of formulating the topical composition may include removing all or a portion of such a film coating. In one example, the method includes removal of all or a portion of the film coating prior to crushing the tablet. For example, the film coating may be removed by contacting the skin/coating with a solvent. The solvent may include an alcohol, sterile sodium chloride, or aqueous solvent such as water. Contacting may include spraying or pouring the solvent onto the tablet to coat the tablet with the solvent. In one method, contacting includes submerging the tablet in an excess of solvent. The contacted tablet may be shaken with the solvent or may be allowed to rest for a sufficient period of time for solvent to act. According to one method, the contacting may be brief such as less than a minute, less than approximately 30 seconds, less than approximately 20 seconds, or between approximately 5 seconds and approximately 20 seconds. In one example, tablets coated in solvent may be quickly washed to remove the film coating after the solvent has contacted the film coating for a suitable period of time. In another method, a tablet including a film coating may be crushed and thereafter mixed with water or solvent, the powder including the film coating may then go into solution. According to a version of the method, the powder and water or solvent may be shaken to accelerate the powder going into solution.

A method of formulating the topical composition may include combining one or more active agents, such as an antimicrobial agent as described herein, and a carrier. In some embodiments, the antimicrobial agent may include bulk powder formats of one or more antibacterial and/or antifungal drugs alone or in combination with the carrier. In some embodiments, bulk powder format may be in addition to powder from capsules, crushed tablets and/or powder for injection. Bulk powder may be referred to in the art as pure powder. In some embodiments, powder for injection may be in addition to powder from capsules, crushed tablets, and/or bulk powder. Combining may include adding all or a portion of the powder to be combined with all or a portion of the carrier and mixing. In some embodiments, all or a portion of the powder may be dispersed, suspended, or dissolved in a liquid to form a paste, or solution, which may include a suspension/dispersion, prior to addition to the carrier. Capsules may be opened to release powder for addition to the carrier directly or wetted or in solution. Capsules may be dissolved or solubilized in the carrier or in a carrier component. In one of an above or another embodiment, all or a portion of the powder may be directly added to all or a portion of the carrier. According to various embodiments, the carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. The carrier may be present in an amount sufficient to obtain the desired amount of active agents per unit weight or volume. The one or more active agents may be mixed dispersed, suspended, solubilized, and/or dissolved with the carrier.

In some embodiments, the method includes formulating a carrier and/or combining the active agents, including the antimicrobial agent, with a carrier comprising a base cream, ointment, gel, lotion, foam solution, or powder. The carrier may include lecithin, phospholipids, glycols, paraffin, fatty acids, carbopols/carbomers, alcohols, lanolin, or combination thereof, for example. In one embodiment, the carrier comprises a sodium chloride 0.9% solution, which may be a sterile sodium chloride 0.9% solution. Some embodiments may include polyethylene glycol (PEG), while other embodiments may be PEG-free. In an above embodiment or another embodiment, the carrier may include a silicon or silicon variant or may be silicon-free. A carrier solution may comprise an aqueous or non-aqueous solution. Example solutions may include water, alcohol, DMSO, saline or sodium chloride, and/or sodium hypochlorite. In some embodiments, the carrier comprises an aqueous solution such as a saline solution. For example, the topical composition may comprise a carrier comprising sodium chloride solution, which may be a sterile solution, an alcohol, water, e.g., purified water, water for irrigation, water for injection, or a sterile water. The carrier may be water soluble/miscible or formulated for water absorption, such as a gel.

In some embodiments, the method includes combining the active agents, including the antimicrobial agent, with a carrier to formulate a topical composition comprising a water-in-oil emulsion or oil-in-water emulsion. For example, the carrier may comprise an emulsion having a cream or lotion format including one or more of acrylate copolymers, alcohol, camphor, carbomer, dimethyl isosorbide, disodium EDTA, dl-alphatocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sorbitol, stearic acid, zinc pyrithione, or combinations thereof.

In some embodiments, the method includes combining the active agents, including the antimicrobial agent, with a carrier to formulate a topical composition comprising an ointment format. For example, the carrier may comprise hydrophilic petrolatum, white petrolatum, hydrophilic ointment, white ointment, anhydrous lanolin, hydrous lanolin, PEG ointment, or combinations thereof. In some embodiments, the method includes combining the active agent with a carrier to formulate a topical composition comprising a gel. The gel may be an aqueous or non-aqueous gel. The gel may include thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof. In some embodiments, the method includes combining the active agent with a carrier to formulate a topical composition comprising a powder. A powder carrier may include lactose or talc, for example. In some embodiments, the method may include imparting the carrier or topical composition formulated therewith with a gas or pressurized propellant to generate a foam format. For example, a propellant such as butane may be used to generate a foam from the carrier or combined carrier and active agent. In various embodiments, the method may include utilizing a carrier or further combining of one or more carrier component additives such as solubilizers, stabilizers (which may include antioxidants), buffers, tonicity modifiers, bulking agents, viscosity enhancers/reducers, surfactants, chelating agents, adjuvants, humectants, preservatives, flavorings, binders, colorants, or combinations thereof.

Further to the above, in some embodiments, the method includes combining the active agents, including the antimicrobial agent, with a commercially available carrier or base vehicle composition for compounding. The carrier may be liquid, semi-liquid, or solid. For example, the carrier may include an aqueous, organic, or inorganic solution, which may include a suspension/dispersion; cream; gel; ointment; lotion; emulsion; powder; or paste. Thus, the method of formulating the topical composition may include addition of crushed antimicrobial tablets or powder thereof to a topical base for compounding to formulate creams, ointments, solutions/irrigations/baths, powders, gels, lotions, or pastes, for example. Non-limiting examples may include Spira-Wash® Gel, Lipoderm®, LoxaSperse®, XyliFos®, Mucolox™, or Versabase® Cream, Goam, Gel, Lotion or Shampoo, manufactured and distributed by PCCA, 9901 South Wilcrest Drive, Houston, Tex. 77099. LoxaSperse® refers to an excipient base powder comprising a blend of micronized xylitol and poloxamers. LoxaSperse® is used as a chemical dispersing or solubilizing agent, thereby improving the solubility and dispersibility of poorly water-soluble active pharmaceutical ingredients (APIs) or agents. LoxaSperse® can be obtained from a bulk source. XyliFos® refers to an excipient base powder comprising xylitol, poloxamer 407, hydroxypropyl betadex, and epigallocatechin gallate. XyliFos® is used as a chemical dispersing or solubilizing agent, thereby improving the solubility and dispersibility of poorly water-soluble active pharmaceutical ingredients (APIs) or agents. In an aspect, infectious agents such as bacteria and fungi can consume or uptake XyliFos®, but cannot digest, process, or excrete XyliFos®. This leads to the infectious agent's death. XyliFos® can be obtained from a bulk source.

In one embodiment, formulating the topical composition comprises combining all or a portion of the active agents, including the antimicrobial agent, and a carrier comprising a commercially available medicated composition. In one example, the method includes combining all or a portion of an antimicrobial agent comprising one or more capsules and/or crushed antimicrobial tablets and commercially available medicated composition. The commercially available medicated composition may comprise a cream, ointment, lotion, suspension/dispersion, solution, irrigation, bath, powder, gel, foam, or paste, for example. Thus, a method of formulating the topical composition may comprise adding a first portion of the active agent comprising bulk powder or crushed tablets to a medicated composition comprising a second portion of the active agent and at least a portion of the carrier. In another embodiment, a method of formulating the topical composition may comprise adding a commercially available medicated composition comprising all or a portion of the antimicrobial agent or other active agent with a carrier. The commercially available medicated composition may comprise a medicated composition for oral administration, topical administration, ophthalmic administration, otic administration, nasal administration, transdermal administration, sublingual administration, or pulmonary administration.

In an embodiment, the method includes combining capsules or crushed tablets of a portion of the antimicrobial agent to another portion of the antimicrobial agent comprising another format, such as a commercially available medicated suspension, solution, ointment, cream, gel, lotion, or powder. In some such embodiments, the carrier may be provided by the commercially available medicated composition. In various embodiments, all or a portion of the antimicrobial agent may be added to one or more components of the carrier. Thereafter, additional carrier components and the remainder of the antimicrobial agent may be added to formulate the topical composition. Other active agents may also be added before, after, or with the antimicrobial agent.

It will be appreciated that unless indicated otherwise, combining or adding active agents to the carrier or components thereof may include combining or adding the active agents together or separately. In one example, combining the active agent and carrier results in a formulation of a topical composition having a different format than that of the carrier, such a commercially manufactured base for compounding or commercially manufactured medicated composition. Examples may include addition of additional carrier components such described above such as thickening agents, thinners, surfactants, carbomers, PEG, hydrocarbons, and/or diluents.

In various embodiments, the antimicrobial agent or portion thereof comprises a commercially available medicated composition comprising a cream, ointment, solution, powder, ground tablet, or gel and the carrier comprises a cream, ointment, lotion, liquid, gel, or paste base. In some embodiments, the method includes combining a first portion of the antimicrobial agent with a second portion of the antimicrobial agent, wherein the first portion comprises a commercially available medicated cream, ointment, solution, powder, e.g., bulk powder, powder for injection, capsule, or ground tablet, or a gel and the second portion comprises a commercially available medicated cream, ointment, solution, powder, e.g., bulk powder, powder for injection, or ground tablet, or a gel. The method may include combining the first and second portions and the carrier together or separately. Is some examples, the carrier may be provided by the combination of the commercially available medicated compositions. The antimicrobial agent may be one or more antifungal components, one or more antibacterial components, or a combination thereof.

In an example, the antimicrobial agent includes an antifungal component comprising itraconazole and the method of formulating the topical composition comprises combining a carrier and a commercially available itraconazole, such as Itraconazole Capsule; Itraconazole Injection Solution; or bulk powder. In one example, the antimicrobial agent comprises an antifungal component comprising itraconazole and the method of formulating the topical composition comprises addition of a crushed itraconazole tablet to a carrier. The itraconazole tablets may comprise commercially available itraconazole 200 mg oral tablets, for example. Itraconazole oral tablets may include colloidal silicon dioxide, crospovidone, hydrogenated vegetable oil, hypromellose, lactose, microcrystalline cellulose, magnesium stearate, propylene glycol, talc, and titanium dioxide, for example. The oral tablets may be crushed and combined with the carrier to formulate a topical comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 2% and approximately 7%, approximately 1%, approximately 2%, approximately 3%, approximately 4%, approximately 5%, less than approximately 5%, or greater than approximately 10% itraconazole by weight. To formulate a topical composition comprising a desired percent by weight itraconazole, the total desired weight of the topical composition is subtracted from the weight of crushed oral itraconazole tablet powder needed to obtain the desired percent by weight itraconazole in a manner similar to that described below with respect to voriconazole.

In some embodiments, the antifungal component or a carrier comprising at least a portion of the antifungal component may comprise a commercially available Itraconazole Oral Solution. For example, Itraconazole Oral Solution may contain 10 mg of itraconazole per mL, solubilized by hydroxypropyl-β-cyclodextrin (400 mg/mL) as a molecular inclusion complex and may have a target pH of 2. Accordingly, the solution may have a low pH of approximately 2. Other ingredients may include hydrochloric acid, propylene glycol, purified water, sodium hydroxide, sodium saccharin, sorbitol, cherry flavor, and caramel flavor. It will be appreciated that oral solutions comprising other flavorings may also be used if they become available. Similarly, other pH adjusting agents may also be used if they become available.

The topical composition comprising itraconazole may include a suitable carrier selected to formulate a topical composition comprising a format selected from a cream, gel, lotion, ointment, emulsion (oil-in-water or water-in-oil), foam, solution, dispersion, or powder, for example, suitable for topical application. In an above or another example, the carrier comprises a commercially available composition comprising a base, such as those described herein. In an above or another example, the carrier may comprise a commercially available medicated composition, such as those described herein. Further to the above, in some methods, carrier components described herein for formulating the formats identified above or elsewhere herein may also be added in addition to or instead of a base composition or additional medicated compositions comprising an ointment, cream, powder, solution, paste, gel, or other format. Additional active agents may include one or more antifungal actives, antibacterial actives, or both. Such additional antifungal component may be present in a combined amount between approximately 0.01% and approximately 20% by weight, such as between approximately 0.01% and approximately 5%, approximately 0.01% and approximately 2% by weight, approximately 0.05% and approximately 2%, approximately 0.1% and approximately 2%, approximately 0.5% and approximately 2%, approximately 1% and approximately 2%, approximately 2% and approximately 7%, or approximately 0.05%, approximately 0.1%, approximately 0.5%, approximately 1%, approximately 2%, approximately 3%, approximately 4%, approximately 5%, less than approximately 5%, or greater than approximately 10% by weight. For example, the method of formulating the topical composition may comprise combining an antifungal component including itraconazole and a second, different, antimicrobial pharmaceutical drug. For example, the method may include combining itraconazole, e.g., itraconazole oral solution, and an antibacterial component comprising the second antimicrobial pharmaceutical drug selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the method includes combining the itraconazole, e.g., itraconazole oral solution or ground tablets, with a medicated composition comprising the antibacterial drug. Such medicated compositions may include ointment, gel, cream, powder (crushed tablets), paste, lotion, or solution formats, for example. Some embodiments may include combining a medicated antibacterial composition selected from one or more of the medicated antibacterial compositions described herein. In another example, the topical composition comprises an antifungal component including itraconazole and a second, different, antimicrobial pharmaceutical drug, comprising an additional antifungal pharmaceutical drug selected from an azole. In one example, the azole includes clotrimazole, econazole, fluconazole, isoconazole, ketoconazole, voriconazole, or combination thereof. In another example, the additional antifungal pharmaceutical drug is selected from antimetabolites, allylamines, morpholine, glucan synthesis inhibitors (echinocandins), polyenes, benoxaaborale, other antifungal/onychomycosis agents, and new classes of antifungal/onychomycosis agents. In another example, the additional antifungal pharmaceutical drug is selected from abafungin, albaconazole, amorolfin, anidulafungin, bifonazole, butenafine, butoconazole, candicidin, caspofungin, ciclopirox, fenticonazole, filipin, flucytosine, griseofulvin, haloprogin, hamycin, isavuconazole, micafungin, miconazole, naftifine, natamycin, omoconazole, oxiconazole, polygodial, posaconazole, ravuconazole, rimocidin, sertaconazole, sulconazole, terbinafine, terconazole, tioconazole, undecylenic acid, or a combination thereof. In another example, the additional antifungal pharmaceutical drug is selected from amphotericin b, nystatin, tolnaftate, or combination thereof. In some embodiments, the method includes combining the itraconazole, e.g., itraconazole oral solution or ground tablets, with a medicated composition comprising the additional antifungal drug. Such medicated compositions may include ointment, gel, cream, powder (crushed tablets), paste, lotion, or solution formats, for example. Some embodiments may include combining a medicated antifungal composition comprising the additional antifungal pharmaceutical drug selected from one or more of the medicated antifungal compositions described herein.

Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%. In one example, the method may include combining crushed itraconazole tablets and/or itraconazole oral solution and a medicated ointment, cream, solution, lotion, or powder comprising one or more additional antifungal pharmaceutical drugs or one or more antibacterial drugs consistent with the present disclosure.

The topical composition comprising itraconazole may be utilized as part of a treatment of a microbial infection. In one example, the topical composition may be topically administered to infected skin forming the outer body covering of a subject or to mucosal tissue of the vagina or anus to treat a microbial infection. For example, the topical composition may comprise a solution or suspension/dispersion for topical administration in a hand or footbath or by irrigation. In another example, the topical composition comprises a nail lacquer for administration to nails. In some embodiments, the topical composition may be utilized as a wound treatment and administered to broken or unbroken skin or mucosal tissue as indicated above and elsewhere herein.

In an example, the antimicrobial agent includes an antifungal component comprising amphotericin and the method of formulating the topical composition comprises combining a carrier and a commercially available amphotericin, such as Amphotericin B injection, Lipid Complex; Amphotericin B Injection, Powder, Lyophilized, for Solution; or bulk powder.

In an example, the antimicrobial agent includes an antifungal component comprising econazole and the method of formulating the topical composition comprises combining a carrier and a commercially available econazole such as an Econazole Nitrate cream. Some methods may include combining bulk powders. In an above or another example, the method includes combining Econazole Nitrate 1.0% Cream or Econazole Nitrate Foam.

In an example, the antimicrobial agent includes an antifungal component comprising fluconazole and the method of formulating the topical composition comprises combining a carrier and commercially available fluconazole, such as Fluconazole in Dextrose Injection Solution; Fluconazole in Sodium Chloride Injection, Solution; Fluconazole Injection; Fluconazole Powder, for Suspension; Fluconazole Tablets; or bulk powder. In another example, the method of formulating the topical composition comprises addition of a crushed fluconazole tablet to a carrier. Less than all the powder of a crushed tablet may be used when the tablet contains more fluconazole than required. More than one crushed tablet may be used when the method includes formulating a topical composition comprising more fluconazole than is in the tablet. The fluconazole tablet may comprise a commercially available fluconazole 100 mg or 200 mg oral tablet. In some embodiments, other strength tablets may be used. In addition to fluconazole, the powder may include a glucose polymer and one or more additional components such as magnesium stearate, povidone, lactose, glycol, oxide, talc, triacetin, or an alcohol. In some embodiments, the powder includes a cellulose such as microcrystalline cellulose and one or more of magnesium stearate, anhydrous dibasic calcium phosphate, or povidone. In one example, the powder may further include croscarmellose sodium. In a further example, the powder may also include an oxide such as silicon dioxide, ferric oxide, aluminum oxide, or combination thereof; a starch, such as sodium starch glycolate, corn starch, or both; sodium lauryl sulfate, lactose, and talc. In various embodiments, the method may comprise crushing one or more fluconazole tablets into a powder for use in the method. Methods may include crushing 100 mg or 200 mg fluconazole tablets, for instance. In some embodiments, powder obtained from a crushed fluconazole tablet may be mixed with components of a carrier composition and, thereafter, additional components may be added to formulate the topical composition as described in more detail elsewhere herein. In an embodiment, powder obtained from the crushed tablet may be added to a carrier for compounding, such as a base for compounding, or a commercially available medicated composition.

In an example, the antimicrobial agent includes an antifungal component comprising ketoconazole and the method of formulating the topical composition comprises combining a carrier and commercially available ketoconazole, such as 50 mg, 100 mg, or 200 mg tablets. In an above or another example, the method includes combining Ketoconazole Foam, Ketoconazole Cream, Ketoconazole Suspension, or Ketoconazole Suspension Shampoo.

In an example, the antimicrobial agent includes an antifungal component comprising nystatin and the method of formulating the topical composition comprises combining a carrier and a commercially available nystatin, such as Nystatin Powder (Topical), or bulk powder. In an above or another example, the method combining Nystatin Cream or Nystatin Ointment.

In one example, the antimicrobial agent includes an antifungal component comprising clotrimazole and the method of formulating the topical composition comprises combining a carrier and a commercially available clotrimazole such as a Clotrimazole Cream, Clotrimazole Lotion, Clotrimazole Liquid, or Clotrimazole Solution. In some formulations, bulk powder or crushed tablets may be used.

In an above or another example, the method includes combining an antifungal component with a carrier wherein the antifungal component comprises a commercially available voriconazole composition such as Voriconazole Ophthalmic Ointment or Voriconazole Oral Suspension. The Voriconazole Oral Suspension may include 45 g powder for oral suspension for reconstitution with water to produce a suspension containing 40 mg/mL voriconazole and including colloidal silicon dioxide, titanium dioxide, xanthan gum, sodium citrate dihydrate, sodium benzoate, anhydrous citric acid, natural orange flavor, and sucrose. In one example, the antimicrobial agent comprises an antifungal component comprising voriconazole and a method of formulating the topical composition comprises addition of a crushed voriconazole tablet to a carrier. The voriconazole tablets may comprise commercially available voriconazole 50 mg, 100 mg, 200 mg oral tablets. In some embodiments, other strength tablets may be used. In addition to voriconazole, the powder may include a glucose polymer and one or more additional components such as magnesium stearate, povidone, lactose, glycol, oxide, talc, triacetin, or an alcohol. In one example, the powder includes croscarmellose sodium, lactose monohydrate, magnesium stearate, povidone and pregelatinized starch. In a further example, the powder may include hypromellose, lactose monohydrate, polyethylene glycol, talc and titanium dioxide. In another example, the powder may include a starch such as pregelatinized starch, a cellulose such as croscarmellose sodium and/or hypromellose. The powder may also include one or more of lactose monohydrate, magnesium stearate, povidone, titanium dioxide, or triacetin. In another example, the powder may include a starch, croscarmellose sodium, lactose monohydrate, magnesium stearate, polyethylene glycol, polyvinyl alcohol, povidone, talc, and titanium dioxide. In another example, the powder may further include talc. In one example, the powder includes lactose monohydrate, pregelatinized starch (corn), croscarmellose sodium, povidone, magnesium stearate and a coating containing polyvinyl alcohol-part hydrolyzed, titanium dioxide, macrogol/PEG and talc. In one embodiment, the powder may include pregelatinized starch, croscarmellose sodium, lactose monohydrate, magnesium stearate, povidone, and a coating containing hypromellose, lactose monohydrate, titanium dioxide and triacetin. In some embodiments, powder obtained from a crushed voriconazole tablet may be mixed with components of a carrier composition and, thereafter, additional components may be added to formulate the topical composition as described in more detail elsewhere herein. In various embodiments, the method comprises combining an antimicrobial agent and a carrier wherein the antimicrobial agent comprises an antibacterial component.

In an example, the antimicrobial agent includes an antibacterial component comprising a vancomycin and the method of formulating the topical composition comprises combining a carrier and commercially available vancomycin. In one example, the method includes combining a vancomycin powder, such as Vancomycin Hydrochloride for Injection, USP, which is a lyophilized powder for preparing intravenous (IV) infusions. The powder may be provided in vials (e.g., bottles) containing the equivalent of 500 mg, 1 g, 5 grams, 10 grams vancomycin base. Some methods may utilize Vancomycin Hydrochloride USP powder for oral solution, equivalent to 3.75 g, 7.5 g or 15 g vancomycin, and diluent, which may be a flavored, e.g., grape-flavored, diluent for reconstitution; or Vancomycin Intravenous Solution, e.g., vancomycin hydrochloride 5 mg/mL, sodium chloride 9 mg/mL.

In an example, the antimicrobial agent includes an antibacterial component comprising ciprofloxacin and the method of formulating the topical composition comprises combining a carrier and a commercially available ciprofloxacin, such Ciprofloxacin Hydrochloride Solution/Drops; Ciprofloxacin Hydrochloride Tablets; Ciprofloxacin Tablets, e.g., 500 mg or 100 mg; Ciprofloxacin Hydrochloride Suspension; Ciprofloxacin Injection, USP, e.g., Ciprofloxacin Injection, USP, 20 mL, 200 mg, 1% and 40 mL or 400 mg, 1%, for intravenous injection and infusion, Premix 100 mL in 5% Dextrose, 200 mg, 0.2% and 200 mL in 5% Dextrose or 400 mg, 0.2%, for intravenous infusion; or bulk powder. In one example, the method of formulating the topical composition comprises addition of a crushed ciprofloxacin tablet to a carrier. The ciprofloxacin tablets may comprise commercially available ciprofloxacin hydrochloride 250 mg, 500 mg, or 750 mg oral tablets, for example. In some embodiments, other strength tablets may be used. In addition to ciprofloxacin the powder may include the powder may include a glucose polymer and one or more additional components such as magnesium stearate, povidone, lactose, glycol, oxide, talc, triacetin, or an alcohol. In one example, the powder includes a starch such as cornstarch, sodium starch glycolate. The powder may also include magnesium stearate and/or lactose. In one embodiment, the powder includes a cellulose such as croscarmellose sodium and/or microcrystalline cellulose. The powder may also include magnesium stearate, povidone, and/or and oxide such as silicone dioxide. In an embodiment, the powder includes a cellulose such as hypromellose and/or microcrystalline cellulose. The powder may also include a starch such as cornstarch and/or sodium starch glycolate. In a further example, the powder also includes magnesium stearate. In still a further example, the powder includes polydextrose, silicon dioxide, titanium dioxide, talc, and/or triacetin. The powder may also include polyethylene glycol. In one embodiment, the powder includes a cellulose such as microcrystalline cellulose. The powder may also include a starch such as sodium starch glycolate. In some embodiments, the powder obtained from a crushed ciprofloxacin tablet may be mixed with components of a base or carrier composition and, thereafter, additional components may be added to formulate the topical composition. In an embodiment, powder obtained from the crushed tablet may be added to a base or carrier for compounding or a commercially available medicated composition as described in more detail elsewhere herein. In various embodiments, the method may comprise crushing one or more ciprofloxacin tablets into a powder. Methods may include crushing 250 mg, 500 mg, 750 mg ciprofloxacin tablets, for instance. In some examples, other strength tablets may be used.

In one example, the antimicrobial agent comprises an antibacterial component comprising levofloxacin and a method of formulating the topical composition comprises addition of a crushed levofloxacin tablet to a carrier. The levofloxacin tablets may comprise commercially available levofloxacin 250 mg, 500 mg, or 750 mg oral tablets, for example. In some embodiments, other strength tablets may be used. In addition to levofloxacin, the powder may include a glucose polymer comprising a starch and/or a cellulose and one or more additional components such as magnesium stearate, povidone, lactose, glycol, oxide, talc, triacetin, an alcohol, or combination thereof. In one example, the powder includes cornstarch, croscarmellose sodium, hypromellose, microcrystalline cellulose, magnesium stearate, polyethylene glycol, povidone and titanium dioxide. In another example, the powder includes sodium starch glycolate, hypromellose, microcrystalline cellulose, magnesium stearate, polyethylene glycol, propylene glycol, povidone, polysorbate, colloidal silicon dioxide, and titanium dioxide. In still another example, the powder includes hypromellose, microcrystalline cellulose, magnesium stearate, polyethylene glycol 6000, crospovidone, talc and titanium dioxide. In yet another example, the powder includes sodium starch glycolate, croscarmellose sodium, hydroxypropyl cellulose, hypromellose, polyethylene glycol 400, povidone K 30, glycerol behenate, lactose monohydrate, colloidal silicon dioxide, titanium dioxide, ferric oxide, and talc. In some embodiments, the powder obtained from a crushed levofloxacin tablet may be mixed with components of a base or carrier composition and, thereafter, additional components may be added to formulate the topical composition. In an embodiment, powder obtained from the crushed tablet may be added to a base or carrier for compounding or a commercially available medicated composition as described in more detail elsewhere herein. In various embodiments, the method may comprise crushing one or more levofloxacin tablets into a powder. Methods may include crushing 250 mg, 500 mg, 750 mg levofloxacin tablets, for instance. In some examples, other strength tablets may be used.

In an example, the antimicrobial agent includes an antibacterial component comprising levofloxacin and the method of formulating the topical composition comprises combining a carrier and a commercially available levofloxacin, such as Levofloxacin Injection, which may be supplied in single-use vials containing a concentrated solution with the equivalent of 500 mg of levofloxacin USP in 20 mL vials and 750 mg of levofloxacin USP in 30 mL vials; Levofloxacin Solution/Drops; Levofloxacin Tablet 250 mg, 500 mg, 750 mg; or bulk powder.

Levofloxacin is commercially available in a bulk powder format as well as in capsule, solution/drops, oral solution, and injection dosage formulations. Levofloxacin is currently administered orally in tablet and oral solution dosage forms. Levofloxacin tablets are commercially available in various strengths including in 200 mg, 500 mg, and 750 mg tablets. Levofloxacin oral solution is commercially available in the United States in 25 mg/mL strength formulations. Such oral solutions also include inactives such as vehicles, solvents, stabilizers, coloring agents, or flavoring agents. In one example, levofloxacin oral solution contains, in addition to levofloxacin, artificial and natural flavors, ascorbic acid, benzyl alcohol, caramel color, glycerin, hydrochloric acid, propylene glycol, purified water, sucralose and sucrose. As another example, levofloxacin oral solution contains the following inactive ingredients: artificial bubble gum flavor, artificial grape flavor, ascorbic acid, benzyl alcohol, glycerin, hydrochloric acid, PFC Bitter Mask F9885, propylene glycol, purified water, saccharin sodium, and sucrose. Sodium hydroxide may be used to adjust pH (between approximately 5.0 to approximately 6.0). Levofloxacin is also currently administered parenterally via intravenous injection. Levofloxacin for injection is commercially available in various strengths and volumes. For example, levofloxacin for injection is currently available in 500 mg/20 mL strength, 20 mL volume single use container, and in 250 mg/50 mL strength, 50 mL, 100 mL, and 150 mL single-use containers.

In an example, the antimicrobial agent includes an antibacterial component comprising azithromycin and the method of formulating the topical composition comprises combining a carrier and a commercially available azithromycin, such as Azithromycin for Injection USP, which may be supplied in lyophilized form under a vacuum in a 10 mL vial equivalent to 500 mg of azithromycin for intravenous administration including sodium hydroxide and 413.6 mg citric acid; Azithromycin for Oral Suspension, USP, which may be supplied for suspension in 100 mg/5 mL or 200 mg/5 mL; Azithromycin Tablets; or bulk powder.

In an example, the antimicrobial agent includes an antibacterial component comprising clindamycin and the method of formulating the topical composition comprises combining a carrier and a commercially available clindamycin, such as Clindamycin Phosphate Cream; Clindamycin Phosphate Gel; Clindamycin Phosphate Suspension; Clindamycin Phosphate Injection Solution; Clindamycin Phosphate for Injection; or bulk powder.

In an example, the antimicrobial agent includes an antibacterial component comprising doxycycline and the method of formulating the topical composition comprises combining a carrier and a commercially available doxycycline, such as Doxycycline Hyclate tablets; Doxycycline Hyclate Tablets; Doxycycline Hyclate Pellets; Doxycycline for Suspension; Doxycycline Hyclate Powder for Suspension; or bulk powder.

In an example, the antimicrobial agent includes an antibacterial component comprising mupirocin and the method of formulating the topical composition comprises combining a carrier and a commercially available mupirocin, such as Mupirocin Ointment; Mupirocin Cream; or bulk powder. Mupirocin Ointment may be a mupirocin 2.0% ointment wherein each gram of ointment contains 20 mg mupirocin in a bland water miscible ointment base (polyethylene glycol ointment, NF) comprising polyethylene glycol 400 and polyethylene glycol 3350. Mupirocin Cream may include mupirocin 2.0% cream USP containing 2.15% w/w mupirocin calcium USP (equivalent to 2% mupirocin free acid) in an oil- and water-based emulsion supplied in 15-gram and 30-gram tubes.

In an example, the antimicrobial agent includes an antibacterial component comprising cefepime and the method of formulating the topical composition comprises combining a carrier and a commercially available cefepime, such as Cefepime Hydrochloride Injection, Powder, for Solution, supplied in 500 mg, 1 g, and 2 g vials; Cefepime Hydrochloride Injection Solution; or bulk powder.

In an example, the antimicrobial agent includes an antibacterial component comprising ceftriaxone and the method of formulating the topical composition comprises combining a carrier and commercially available ceftriaxone, such as Ceftriaxone for Injection Powder, Ceftriaxone for Injection Solution, or bulk powder. In addition to ceftriaxone, the ceftriaxone powder may include sodium. Ceftriaxone for Injection Solution may include a dextrose diluent and pH modifiers such as sodium hydroxide and/or hydrochloric acid to provide a pH in the range of 6.0 and 8.0. Ceftriaxone for Injection Solution may be provided containers including 1 g equivalent of ceftriaxone, iso-osmotic with approximately 1.9 g Dextrose Hydrous, USP, added; 2 g equivalent of ceftriaxone, iso-osmotic with approximately 1.2 g Dextrose Hydrous, USP, added.

In example, the antimicrobial agent includes an antibacterial component comprising nitrofurantoin and a method of formulating the topical composition comprises combining nitrofurantoin and a carrier. Additional antimicrobial agent, other active agents, and/or excipients may also be used. Nitrofurantoin may include a commercially available nitrofurantoin format or bulk powder. In one example, nitrofurantoin comprises commercially available nitrofurantoin capsules. The nitrofurantoin capsules may comprise 25 mg, 50 mg, and 100 mg strength capsules. A 100 mg nitrofurantoin capsule may include a hard gelatin capsule shell containing the equivalent of 100 mg of nitrofurantoin in the form of 25 mg of nitrofurantoin macrocrystals and 75 mg of nitrofurantoin monohydrate. The capsule may also contain carbomer 934P, corn starch, compressible sugar, D&C Yellow No. 10, edible gray ink, FD&C Blue No. 1, FD&C Red No. 40, gelatin, lactose, magnesium stearate, povidone, talc, and titanium dioxide. In another embodiment, nitrofurantoin capsules may comprise 25 mg, 50 mg, and 100 mg strength capsules including 25 mg, 50 mg, or 100 mg nitrofurantoin microcrystals. The capsule may include edible black ink, gelatin, lactose, starch, talc, titanium dioxide, and may contain FD&C Yellow No. 6 and D&C Yellow No. 10.

In some embodiments, the topical composition may be formulated to include nitrofurantoin oral suspension. Nitrofurantoin oral suspension is available in 25 mg/5 mL liquid suspension for oral administration. Nitrofurantoin Oral Suspension USP may contain carboxymethylcellulose sodium, anhydrous citric acid, glycerin, magnesium aluminum silicate, methylparaben, natural and artificial flavor (peach), propylparaben, purified water, saccharin sodium, sodium citrate, and sorbitol solution.

In example, the antimicrobial agent includes an antibacterial component comprising tetracycline and a method of formulating the topical composition comprises combining tetracycline and a carrier. Additional antimicrobial agent, other active agents, and/or excipients may also be used. Tetracycline may include a commercially available tetracycline format or bulk powder. In one example, tetracycline comprises commercially available tetracycline capsules. Capsules may include 250 mg or 500 mg tetracycline hydrochloride and inactive ingredients including lactose, magnesium stearate, and sodium lauryl sulfate or colloidal silicon dioxide, pregelatinized starch and stearic acid.

In some embodiments, the topical composition is formulated with tetracycline ointment. Tetracycline ointment is available in 30 mg per gram strength and includes inactive ingredients acetic acid, ascorbic acid, chlorhexidine gluconate, cholecalciferol, dimethyl sulfoxide, dipropylene glycol, glucono delta lactone, glycerin, histidine, hydroxyethylcellulose, magnesium stearate, methylparaben, sodium hydroxide, sorbic acid, steric acid, water.

In example, the antimicrobial agent includes an antibacterial component comprising cefixime and a method of formulating the topical composition comprises combining cefixime and a carrier. Additional antimicrobial agent, other active agents, and/or excipients may also be used. Cefixime may include a commercially available cefixime format or bulk powder. In one example, cefixime comprises commercially available chewable tablet containing either 100 mg or 150 mg or 200 mg of cefixime as trihydrate. The tablet may additionally contain the following inactive ingredients: aspartame, colloidal silicon dioxide, crospovidone, low substituted hydroxypropyl cellulose, magnesium stearate, mannitol, and flavoring such as fantasy flavor perm seal and tutti frutti flavor. In one example, cefixime comprises a commercial oral tablet, such as a 400 mg oral cefixime tablet USP including dibasic calcium phosphate, hypromellose, lactose monohydrate, magnesium stearate, microcrystalline cellulose, polyethylene glycol, pregelatinized starch, titanium dioxide, and triacetin. In another embodiment, the cefixime comprises a commercial capsule, such as a 400 mg cefixime capsule including colloidal silicon dioxide, crospovidone, low substituted hydroxy propyl cellulose, magnesium stearate, and mannitol. The capsule shell may contain ferric oxide black, ferric oxide red, gelatin, potassium hydroxide, propylene glycol, shellac, sodium lauryl sulfate, and titanium dioxide. In an example, the cefixime comprises commercial cefixime powder for oral suspension USP, 100 mg/5 mL, 200 mg/5 mL, and 500 mg/5 mL, including the following inactive ingredients: colloidal silicon dioxide, sodium benzoate, sucralose (in 500 mg/5 mL strength), sucrose, and xanthan gum. The powder may also include flavoring, such as strawberry flavoring.

In an example, the antimicrobial agent includes an antibacterial component comprising streptomycin and the method of formulating the topical composition comprises combining a carrier and a commercially available streptomycin, such as Streptomycin for Injection USP, which may be supplied in 1 g vials; Streptomycin Injection, Powder, Lyophilized, for Solution; or bulk powder.

In an example, the antimicrobial agent includes an antibacterial component comprising sulfamethoxazole/trimethoprim and the method of formulating the topical composition comprises combining a carrier and a commercially available sulfamethoxazole/trimethoprim, such as Sulfamethoxazole and Trimethoprim Tablets; Sulfamethoxazole and Trimethoprim Injection; Sulfamethoxazole and Trimethoprim Suspension; or bulk powder.

In an embodiment, the method of formulating the topical composition comprises combining a carrier and a commercially available Azithromycin Oral Suspension, Ciprofloxacin Cream, Ciprofloxacin Ointment, Clindamycin Cream, Clindamycin Ointment, Clindamycin Gel, Gentamycin drops, Gentamycin Spray, Gentamycin Cream, Gentamycin Ointment, Levofloxacin Injection Solution, Levofloxacin Drops, Mupirocin Ointment, Mupirocin Cream, Tobramycin Ophthalmic Ointment, Tobramycin Ophthalmic Drops, and/or Tobramycin Otic Drops.

In one example, the antimicrobial agent comprises an antibacterial component comprising linezolid and a method of formulating the topical composition comprises addition of a crushed linezolid tablet to a carrier. The linezolid tablets may comprise commercially available linezolid 600 mg oral tablets, for example. In some embodiments, other strength tablets may be used. In addition to linezolid the powder may include a glucose polymer comprising a starch and/or a cellulose and one or more additional components such as magnesium stearate, povidone, lactose, glycol, oxide, talc, triacetin, an alcohol, or combination thereof. In various examples, the powder includes a starch and a cellulose. In other embodiments, the powder does not include a starch. In one example, the powder includes croscarmellose sodium, diethyl phthalate, ethyl cellulose, pregelatinized starch, sodium starch glycolate, mannitol, colloidal silicon dioxide, povidone, copovidone, cospovidine, sodium stearyl fumarate, hypromellose, polyethylene glycol, titanium dioxide, magnesium stearate, microcrystalline cellulose, talc, hydroxypropyl cellulose, polydextrose, triacetin, carnauba wax, lactose monohydrate, polacrilin potassium, sodium lauryl sulfate, or a combination thereof. In one example, the powder includes a starch comprising pregelatinized starch, a cellulose comprising hypromellose, a sugar alcohol comprising mannitol, a glycol comprising polyethylene glycol, an oxide comprising titanium dioxide and/or colloidal silicon dioxide, a povidone comprising copovidone, and sodium stearyl fumarate. In another example, the powder includes a cellulose comprising croscarmellose sodium, ethyl cellulose, hypromellose, and/or microcrystalline cellulose, magnesium stearate, povidone, an oxide comprising silicon dioxide and/or titanium dioxide, talc, and diethyl phthalate. In yet another example, the powder comprises a cellulose comprising microcrystalline cellulose, hydroxypropyl cellulose, and/or hypromellose, polydextrose, magnesium stearate, crospovidone, polyethylene glycol, titanium dioxide, and triacetin. In one embodiment, the powder comprises a starch selected from cornstarch and/or sodium starch glycolate, a cellulose comprising microcrystalline cellulose, hypromellose, and/or hydroxypropylcellulose, magnesium stearate, polyethylene glycol, titanium dioxide, and carnauba wax. In another example, the powder comprises hypromellose, lactose monohydrate, magnesium stearate, polyethylene glycol, colloidal silicon dioxide, titanium dioxide, polacrilin potassium, and carnauba wax. In one embodiment, the powder comprises a cellulose comprising croscarmellose sodium and/or hypromellose, lactose monohydrate, magnesium stearate, polyethylene glycol 400, povidone and titanium dioxide. In another embodiment, the powder comprises a cellulose comprising croscarmellose sodium and/or microcrystalline cellulose, polydextrose, magnesium stearate, polyethylene glycol, sodium lauryl sulfate, colloidal silicon dioxide, titanium dioxide and triacetin. In some embodiments, the powder obtained from a crushed linezolid tablet may be mixed with components of a base or carrier composition and, thereafter, additional components may be added to formulate the topical composition. In an embodiment, powder obtained from the crushed tablet may be added to a base or carrier for compounding or a commercially available medicated composition as described in more detail elsewhere herein.

Linezolid for oral suspension may be supplied as a flavored, e.g., orange-flavored, granule/powder for constitution into a suspension for oral administration. Depending on the strength and constitution ratio, following constitution, each 5 mL typically contains approximately 100 mg of linezolid. Inactive ingredients may include sucrose, citric acid, sodium citrate, microcrystalline cellulose and carboxymethylcellulose sodium, aspartame, xanthan gum, mannitol, sodium benzoate, colloidal silicon dioxide, sodium chloride, and flavors. Sodium (Na+) content may be approximately 8.52 mg per 5 mL (0.4 mEq per 5 mL). For example, Zyvox oral suspension is a white fluid, which is orange flavored. It is supplied in an amber glass bottle with a screw cap. Zyvox oral suspension may contain 20 mg of linezolid per 1 mL (total 150 mL), sucrose, mannitol, microcrystalline cellulose, carmellose sodium, aspartame, anhydrous colloidal silica, sodium citrate, xanthan gum, sodium benzoate, citric acid anhydrous, and sodium chloride. The granules may be flavored with Mafco magnasweet, orange flavor, orange cream flavor, Sweet-am powder, vanilla flavor and peppermint flavor.

Linezolid injection may be supplied as a ready-to-use sterile isotonic solution for intravenous infusion. For example, each container may contain 600 mg of linezolid in 300 mL of a clear, colorless to slightly yellow aqueous solution. Inactive ingredients may include: citric acid anhydrous USP 1.92 mg/mL, sodium chloride USP 9 mg/mL, sodium hydroxide NF 0.76 mg/mL, and water for injection USP. Sodium hydroxide NF and/or hydrochloric acid NF are typically used to adjust the pH. The sodium (Na+) content may be approximately 3.98 mg/mL (52 mEq/300-mL container). Zyvox for injection is supplied as a ready-to-use sterile isotonic solution for intravenous infusion. Each mL contains 2 mg of linezolid. Inactive ingredients are sodium citrate, citric acid, and dextrose in an aqueous vehicle for intravenous administration. The sodium (Na+) content is approximately 0.38 mg/mL (5 mEq per 300-mL bag; 3.3 mEq per 200-mL bag; and 1.7 mEq per 100-mL bag).

In one embodiment, the method includes mixing linezolid oral suspension with a carrier component and/or one or more active agents, such as an antibacterial component or an antifungal component. An example, oral suspension may include inactive ingredients such as sucrose, citric acid, sodium citrate, microcrystalline cellulose and carboxymethylcellulose sodium, aspartame, xanthan gum, mannitol, sodium benzoate, colloidal silicon dioxide, sodium chloride, or combination thereof.

In an embodiment, the topical composition comprises a treatment solution for a footbath comprising a commercially available clindamycin solution and a carrier comprising a diluent, such as any diluent described herein. In one example, the clindamycin solution comprises a 1% clindamycin solution. In another example, the treatment solution comprises approximately 30 mL or 60 mL 1% clindamycin solution with a suitable amount of diluent for the footbath.

In an embodiment, the topical composition comprises a treatment solution for a footbath comprising a commercially available erythromycin solution and a carrier comprising a diluent, such as any diluent described herein. In one example, the erythromycin solution comprises a 2% erythromycin solution. In another example, the treatment solution comprises approximately 30 mL or 60 mL 2% erythromycin solution with a suitable amount of diluent for the footbath.

In an embodiment, the topical composition comprises a treatment solution including a pharmaceutically effective amount of the antibacterial component levofloxacin and a carrier comprising a diluent, such as any suitable diluent for topical administration. In various embodiments, the treatment solution is compounded from commercially available levofloxacin bulk powder, ground levofloxacin tablets, levofloxacin oral solution, levofloxacin for injection, or a combination thereof. In an aspect, a suitable diluent comprises one or more aqueous diluents. In one aspect, all or a portion of the diluent may be selected from water, sodium chloride, saline, Dakin's solution, sodium hypochlorite, or combination thereof. In one example, the diluent comprises sterile water for irrigation. In various embodiments, the treatment solution comprises levofloxacin oral solution. For example, the treatment solution may comprise commercially available oral solution of levofloxacin and diluent, such as levofloxacin 125 mg/5 mL (25 mg/mL) solution. In a further aspect, a method of treating a bacterial infection may include topically administering the levofloxacin oral solution to an affected exterior body region such as an outer body surface such as skin or to mucosal lining of the vagina or anus. The topical administration may include a bathing administration, which may include submerging all or a portion of an affected body region or surface in the treatment solution, e.g., in a bath application, irrigating all or a portion of the affected body region or surface with the treatment solution in an irrigation application, or otherwise contacting all or a portion of the affected body region or surface with the treatment solution, such as by spraying the treatment solution onto all or a portion of the affected body region or surface in a topical spray application.

In an aspect, a treatment solution may contain between approximately 1 mg and approximately 2000 mg, such as between approximately 100 mg and approximately 1000 mg, approximately 250 mg and approximately 750 mg, approximately 250 mg and approximately 500 mg, or approximately 750 mg levofloxacin in an administration volume. According to various embodiments, an administration volume may be approximately 20 mL to approximately 4 L, such as approximately 30 mL to approximately 2 L, approximately 40 mL to approximately 1.5 L, or approximately 40 mL to approximately 1 L. Administration volumes greater than 4 L may also be used, e.g. greater than 5 L, greater than 10 L, greater than 15 L, or greater than 20 L.

In an aspect, a treatment solution may include between approximately 0.01 mg/mL and approximately 24 mg/mL levofloxacin, such as approximately 0.5 mg/mL and approximately 2 mg/mL, approximately 1 mg/mL and approximately 10 mg/mL, approximately 5 mg/mL and approximately 13 mg/mL, or approximately 10 mg/mL and approximately 20 mg/mL. In an aspect, the treatment solution may include greater than a 25 mg/mL levofloxacin concentration.

In an aspect, a topical composition comprises a treatment solution including a pharmaceutically effective amount of the antibacterial component linezolid and a carrier comprising a diluent, such as any suitable diluent for topical administration. In various embodiments, the treatment solution is compounded from commercially available linezolid bulk powder, ground linezolid tablets, linezolid solution, linezolid solution of injection or infusion, or a combination thereof. In an aspect, a suitable diluent comprises one or more aqueous diluents. In one aspect, all or a portion of the diluent may be selected from water, sodium chloride, saline, Dakin's solution, sodium hypochlorite, or combination thereof. In one example, the diluent comprises sterile water for irrigation. In various embodiments, the treatment solution comprises all or a portion of a linezolid tablet dissolved, dispersed, or suspended in diluent. For example, the treatment solution may comprise commercially available linezolid tablets and diluent, such as linezolid 600 mg tablets, whereby the linezolid tablets may have be ground into a fine powder and combined with the diluent. In a further aspect, a method of treating a bacterial infection may include topically administering the treatment solution to an affected exterior body region such as an outer body surface such as skin or to mucosal lining of the vaginal orifice or anus. The topical administration may include a bathing administration, which may include submerging all or a portion of an affected body region or surface in the treatment solution, e.g., in a bath application, irrigating all or a portion of the affected body region or surface with the treatment solution in an irrigation application, or otherwise contacting all or a portion of the affected body region or surface with the treatment solution, such as by spraying the treatment solution onto all or a portion of the affected body region or surface in a spray application.

In an aspect, a treatment solution may contain between approximately 1 mg and approximately 2000 mg, such as between approximately 100 mg and approximately 1000 mg, approximately 150 mg and approximately 750 mg, approximately 200 mg and approximately 500 mg, such as approximately 200 mg, approximately 250 mg, approximately 300 mg, approximately 350 mg, approximately 400 mg, approximately 500 mg, approximately 550 mg, or approximately 600 mg linezolid in an administration volume. According to various embodiments, an administration volume may be between approximately 20 mL and approximately 4 L, such as approximately 30 mL and approximately 2 L, approximately 40 mL and approximately 1.5 L, or approximately 40 mL and approximately 1 L.

In an aspect, a treatment solution may include between approximately 0.01 mg/mL and approximately 2 mg/mL linezolid, such as approximately 0.075 mg/mL and approximately 1 mg/mL, approximately 0.1 and approximately 0.5 mg/mL, approximately 0.1 and approximately 0.4 mg/mL, approximately 0.15 mg/mL and approximately 0.2 mg/mL, approximately 0.075 mg/mL and approximately 0.15 mg/mL. In an aspect, the treatment solution may include greater than a 0.15 mg/mL linezolid concentration.

In one embodiment, the topical composition comprises a treatment solution including an antimicrobial agent including an antifungal component comprising the antifungal component itraconazole and a carrier comprising a diluent, such as any suitable diluent for topical administration. In various embodiments, the treatment solution is compounded from commercially available itraconazole bulk powder, ground itraconazole tablets, itraconazole oral solution, or a combination thereof. In an aspect, a suitable diluent comprises one or more aqueous diluents. In one aspect, all or a portion of the diluent may be selected from water, sodium chloride, saline, Dakin's solution, sodium hypochlorite, or combination thereof. In one example, the diluent comprises sterile water for irrigation, sterile water, or water for injection.

In one embodiment, the topical composition comprises a treatment solution comprising itraconazole oral solution. For example, the treatment solution may comprise commercially available oral solution of itraconazole and diluent, such as itraconazole 10 mg/mL solution, which may also contain hydrochloric acid, propylene glycol, purified water, sodium hydroxide, sodium saccharin, sorbitol, cherry flavor, and caramel flavor. In a further aspect, a method of treating a fungal infection, which may include preventing, may include topically administering the itraconazole oral solution to an affected exterior body region such as an outer body surface such as skin or to mucosal lining of the vaginal orifice or anus. In various embodiments, the itraconazole oral solution may be directly applied to skin or mucosal tissue. In some embodiments, a pH adjusting agent may be added to increase the pH, e.g., to approximately 3 or less than approximately 3, approximately 4 or less than 4, approximately 5 or less than approximately 5, approximately 6 or less than approximately 6, or approximately 7 or less than approximately 7. The topical administration may include a bathing administration, which may include submerging all or a portion of an affected body region or surface in the itraconazole oral solution, e.g., in a bath application, irrigating all or a portion of the affected body region or surface with the itraconazole oral solution in an irrigation application, or otherwise contacting all or a portion of the affected body region or surface with the itraconazole oral solution, such as by spraying the oral solution onto all or a portion of the affected body region or surface in a topical spray application. In some examples, the skin or mucosal tissue may comprise a broken or intact tissue. In one embodiment, itraconazole oral solution may be utilized as a nail lacquer. Consistent with the present disclosure, some embodiments may include additional antifungal actives, antibacterial actives, or additional actives agents combined with the itraconazole oral solution. Similarly, some embodiments may include combining carrier or components thereof with the itraconazole oral solution.

In one embodiment, a method of formulating the topical composition comprises combining itraconazole oral solution with a carrier to formulate a treatment solution. For example, the method may comprise combining itraconazole 10 mg/mL solution and a diluent. The diluent may be any suitable diluent for topical administration. For example, the diluent may be an aqueous or non-aqueous diluent. In one example, a suitable diluent comprises one or more aqueous diluents. All or a portion of the diluent may be selected from water, sodium chloride, saline, hydrogen peroxide, Dakin's solution, sodium hypochlorite, or combination thereof. In one example, the diluent comprises sterile water for irrigation, sterile water, or water for injection. In a further aspect, a method of treating a fungal infection, which may include preventing, may include topically administering the topical composition to an affected exterior body region such as an outer body surface such as skin or to mucosal lining of the vagina or anus. The topical administration may include a bathing administration, which may include submerging all or a portion of an affected body region or surface in the topical solution, e.g., in a bath application, irrigating all or a portion of the affected body region or surface with the topical solution in an irrigation application, or otherwise contacting all or a portion of the affected body region or surface with the topical solution, such as by spraying the topical solution onto all or a portion of the affected body region or surface in a topical spray application. In some examples, the skin or mucosal tissue may comprise a broken or intact tissue. In one embodiment, topical composition may comprise itraconazole oral solution combined with a carrier to formulate a nail lacquer composition as described herein. Consistent with the present disclosure, some embodiments may include additional antifungal actives, antibacterial actives, or additional actives agents combined with the itraconazole oral solution. Similarly, some embodiments may include combining carrier or components thereof with the itraconazole oral solution.

In an aspect, a treatment solution may contain between approximately 10 mg and approximately 300 mg, such as between approximately 40 mg and approximately 250 mg, approximately 50 mg and approximately 200 mg, approximately 50 mg and approximately 125 mg, approximately 150 mg and approximately 200 mg itraconazole in an administration volume. In an aspect, a treatment solution for a small treatment area may contain between approximately 1 mg and approximately 30 mg, such as between approximately 5 mg and approximately 25 mg, approximately 10 mg and approximately 25 mg, approximately 10 mg and approximately 25 mg, approximately 15 mg and approximately 20 mg itraconazole in an administration volume.

In various embodiments, a method of formulating the topical composition may comprise combining itraconazole oral solution, 10 mg/mL, and a diluent, wherein the itraconazole oral solution is combined in an amount between approximately 1 mL and approximately 25 mL in an administration volume. For example, the amount of itraconazole oral solution in an administration volume may be between approximately 1 mL and approximately 3 mL, approximately 3 mL and approximately 25 mL, approximately 5 mL and approximately 20 mL, approximately 5 mL and approximately 10 mL, approximately 10 mL and approximately 20 mL, approximately 15 mL and approximately 25 mL, or greater than approximately 1 mL, approximately 2 mL, approximately 5 mL, approximately 10 mL, approximately 15 mL, approximately 20 mL, or less than approximately 25 mL.

According to various embodiments, an administration volume may be between approximately 20 mL and approximately 4 L, such as approximately 30 mL and approximately 2 L, approximately 40 mL and approximately 1.5 L, or approximately 40 mL and approximately 1 L. Administration volumes greater than 4 L may also be used, e.g. greater than 5 L, greater than 10 L, greater than 15 L, or greater than 20 L. In some embodiments, an administration volume for a small treatment area may comprise between approximately 1 mL and approximately 5 mL, such as approximately 1 mL and approximately 4 mL, approximately 1 mL and approximately 3 mL, approximately 2 mL and approximately 5 mL, approximately 2 mL and approximately 3 mL, or between approximately 3 mL and approximately 5 mL.

In an aspect, a treatment solution may include between approximately 0.01 mg/mL and approximately 9.5 mg/mL itraconazole, such as between approximately 0.5 mg/mL and approximately 9 mg/mL, approximately 1 mg/mL and approximately 8 mg/mL, approximately 2 mg/mL and approximately 7 mg/mL, or approximately 10 mg/mL and approximately 20 mg/mL. In an embodiment, the treatment solution may include greater than a 10 mg/mL itraconazole concentration.

In some embodiments, the method may comprise combining itraconazole, e.g., itraconazole oral solution, with a carrier formulate a topical composition comprising a cream, lotion, gel, or paste. For example, itraconazole oral solution may be combined with a base cream, base lotion, base gel, base ointment, or base powder. In some embodiments, carrier components such as thickening or gelling agents may be combined with the itraconazole oral solution. Additional carrier components, such as those described herein, may also be utilized to formulate a desired consistency, feel, penetration, coverage, dispersion, or the like. In a further aspect, a method of treating a fungal infection, which may include preventing, may include topically administering the topical composition to an affected exterior body region such as an outer body surface such as skin or to mucosal lining of the vagina or anus. The topical composition may be contacted to all or a portion of the affected body region or surface, such as by covering or spreading the topical composition onto all or a portion of the affected body region or surface. In some examples, the skin or mucosal tissue may comprise a broken or intact tissue. Consistent with the present disclosure, some embodiments may include additional antifungal actives, antibacterial actives, or additional actives agents combined with the itraconazole, e.g., itraconazole oral solution. Similarly, some embodiments may include combining a carrier, which may include multiple carriers, with the itraconazole oral solution.

In various embodiments, the method of formulating the topical composition comprises combining itraconazole oral solution and an additional azole; itraconazole oral solution and an additional antifungal active drug; itraconazole oral solution and an antibacterial component comprising one or more antibacterial active drugs; itraconazole oral solution and an additional active agent according to the methods identified below or elsewhere herein; or combination thereof. In some examples, the method may include combining one or more commercially available medicated compositions comprising one or more additional actives. The method may further include combining a carrier as described herein.

In various embodiments, nitrofurantoin may be combined with a carrier to formulate a solution for topical administration to skin, mucosal tissue, ear, respiratory tract, wound, limb, torso, mouth, or scalp for example. The nitrofurantoin may comprise nitrofurantoin bulk powder, capsules, or oral suspension, for example. In various embodiments, nitrofurantoin oral suspension may be used to formulate shampoos, bath solutions, irrigation solutions, creams, lotions, or gels, for example, for topical administration to skin, vaginal orifice, anus, scalp, limbs, torso, nails, or wounds. In one embodiment, oral suspension may be used to formulate a nebulization solution for deliver to the upper or lower respiratory tract.

In various embodiments, nitrofurantoin may be present in an amount between approximately 10 mg and approximately 500 mg, such as between approximately 25 mg and approximately 400 mg or between approximately 50 mg and approximately 100 mg, approximately 100 mg and approximately 150 mg, approximately 150 mg and approximately 200 mg, approximately 200 mg and approximately 250 mg, approximately 250 mg and approximately 300 mg, approximately 300 mg and approximately 350 mg, approximately 350 mg and approximately 400 mg.

In various embodiments, the topical composition comprises an antimicrobial agent comprising an antibacterial component including cefixime and/or nitrofurantoin. A method of formulating the topical composition may comprises combining a carrier and cefixime and/or nitrofurantoin. The cefixime and/or nitrofurantoin may comprise bulk powder commercially available cefixime and/or nitrofurantoin, such as cefixime capsules, cefixime oral tablets, cefixime oral chewable tablets, cefixime powder for oral suspension, nitrofurantoin capsules, or nitrofurantoin oral suspension. In one example, the method may utilize cefixime 100 mg, 200 mg, or 150 mg oral chewable tablets, cefixime 400 mg oral tablets, nitrofurantoin 25 mg, 50 mg, or 100 mg capsules, or nitrofurantoin 25 mg/g oral suspension.

In an aspect, the topical composition may include between approximately 0.01 mg/mL and approximately 400 mg/mL cefixime and/or nitrofurantoin, such as approximately 0.075 mg/mL and approximately 1 mg/mL, approximately 0.1 mg/mL and approximately 1 mg/mL, approximately 0.1 and approximately 2 mg/mL, approximately 2 mg/mL and approximately 10 mg/mL, approximately 10 mg/mL and approximately 50 mg/mL, approximately 10 mg/mL and approximately 100 mg/mL, approximately 50 mg/mL and approximately 150 mg/mL, approximately 100 and approximately 200 mg/mL, approximately 200 mg/mL and approximately 300 mg/mL, and approximately 300 mg/mL and approximately 400 mg/mL. In an aspect, the topical composition may include greater than approximately 0.075 mg/mL, approximately 0.15 mg/mL, approximately 0.2 mg/mL, approximately 0.4 mg/mL, approximately 0.5 mg/mL, approximately 1 mg/mL, approximately 10 mg/mL, approximately 20 mg/mL, approximately 30 mg/mL, approximately 50 mg/mL, approximately 75 mg/mL, approximately 100 mg/mL, approximately 200 mg/mL, approximately 250 mg/mL, approximately 300 mg/mL, or approximately 400 mg/mL cefixime and/or nitrofurantoin.

In an aspect, an administration volume of the topical composition may contain between approximately 100 mg and approximately 45000 mg, such as between approximately 200 mg and approximately 425 mg, approximately 150 mg and approximately 425 mg, approximately 200 mg and approximately 400 mg, such as approximately 100 mg, approximately 15000 mg, approximately 200 mg, approximately 250 mg, approximately 300 mg, approximately 350 mg, approximately 375 mg, approximately 400 mg, approximately 410 mg, approximately 425 mg, or approximately 400 mg cefixime. The topical composition may be administered 1 to 2 times daily. A daily dosage may comprise between approximately 200 mg and approximately 800 mg cefixime, or between approximately 400 mg and approximately 700 mg cefixime provided in 1 to 2 administration volumes. In some instances, daily dosages may be administered in more than 2 administrations.

In an aspect, an administration volume of the topical composition may contain between approximately 10 mg and approximately 250 mg, such as between approximately 25 mg and approximately 200 mg, approximately 50 mg and approximately 200 mg, or approximately 100 mg and approximately 200 mg, such as approximately 25 mg, approximately 50 mg, approximately 75 mg, approximately 100 mg, approximately 125 mg, approximately 150 mg, approximately 175 mg, approximately 200 mg, or approximately 225 mg nitrofurantoin. A daily dosage may comprise between approximately 50 mg and approximately 600 mg nitrofurantoin, or between approximately 100 mg and approximately 400 mg nitrofurantoin provided in 1 to 2 administrations, e.g., in 1 to 2 administration volumes.

According to various embodiments, the topical composition comprising a treatment solution including cefixime and/or nitrofurantoin in a spray, bath, or irrigation format may include an administration volume between approximately 20 mL and approximately 4 L, such as approximately 30 mL and approximately 2 L, approximately 40 mL and approximately 1.5 L, or approximately 40 mL and approximately 1 L. A treatment solution for a bathing administration may include an administration volume between approximately 500 mL and approximately 10 L, approximately 1 L and approximately 8 L, approximately 1 L and approximately 4 L, or approximately 3 L and approximately 8 L, as examples.

Topical composition comprising cefixime and/or nitrofurantoin may comprise cream, lotion, paste, ointment, or similar format applied by contact to skin, or mucosal tissue with respect to anal or vaginal administration. In some embodiments, the topical composition may be formulated in a shampoo carrier for administration in a shampoo. In some formats, the composition may be administered to an infected or target area via spray, drops, wash, swab, sponge, absorbent dressing, coating (e.g., a nail lacquer), soaking, submerging, footbath, instillation or irrigation. Embodiments comprising a nail lacquer formulation may be applied directly to nails, to treat a bacterial or fungal nail infection.

In some embodiments, the method may comprise combining cefixime and/or nitrofurantoin with a carrier to formulate a topical composition comprising a cream, lotion, gel, or paste. For example, cefixime and/or nitrofurantoin powder, e.g., from a capsule or ground tablet, or suspension may be combined with a base cream, base lotion, base gel, base ointment, or base powder. In some embodiments, carrier components such as thickening or gelling agents may be combined with the powder or suspension. Additional carrier components, such as those described herein, may also be utilized to formulate a desired consistency, feel, penetration, coverage, dispersion, or the like. In a further aspect, a method of treating a bacterial infection, which may include preventing, may include topically administering the topical composition comprising cefixime and/or nitrofurantoin to an affected exterior body region such as an outer body surface such as skin or to mucosal lining of the vagina or anus, or oral cavity. The topical composition may be contacted to all or a portion of the affected body region or surface, such as by covering or spreading the topical composition onto all or a portion of the affected body region or surface. In some examples, the skin or mucosal tissue may comprise a broken or intact tissue. Consistent with the present disclosure, some embodiments may include additional antibacterial actives, antifungal actives, or additional actives agents combined with the cefixime and/or nitrofurantoin. Similarly, some embodiments may include combining a carrier, which may include multiple carriers, with the cefixime and/or nitrofurantoin.

The topical composition comprising cefixime and/or nitrofurantoin may be utilized as part of a treatment of a microbial infection. The topical composition comprising cefixime and/or nitrofurantoin may be utilized in a treatment methodology to treat or prevent a bacterial infection. The bacterial infection may be a Gram-negative and/or Gram-positive bacteria, which may include MDRO organisms or strains thereof, such as *Acinetobacter baumanni*, Group D *Streptococci*, VIRIDANS group *streptococci*, *Citrobacter*, *Escherichia coli*, *Klebsiella*, Enterococci, or *Staphylococcus aureus*.

The topical composition may comprise a solution, which may comprise a suspension, dispersion, or mixture; cream; oil; gel; ointment; lozenge; or gum as also described herein. Such dosage forms may be delivered, for example, by application, dissolution, or irrigation at a body cavity or orifice or topically to skin or a mucosal surface, e.g., drops applied to an ear, or a mouth rinse, wash, or gargle composition. In one example, the topical composition including cefixime and/or nitrofurantoin may be topically administered to infected skin forming the outer body covering of a subject or to mucosal tissue of the vagina, oral cavity, respiratory tract, lungs, ear canal, or anus to treat a microbial infection. For example, the topical composition may comprise a solution or suspension for topical administration in an ear, hand, foot, mouth using a bath or irrigation. In another example, the topical composition comprises a nail lacquer for administration to nails. In some embodiments, the topical composition may be utilized as a wound treatment and administered to broken or unbroken skin or mucosal tissue as indicated above and elsewhere herein.

In various embodiments, a topical composition comprising cefixime and/or nitrofurantoin disclosed herein may comprise a solution for nasal irrigation, e.g., via Neil-Med® Irrigation Delivery; medium particle size nasal delivery, e.g., via NasoNeb® Nasal Nebulizer; small particle size nasal delivery, e.g., via PARI SinuStar™; small particle size lung (respiratory) delivery, e.g., via Omron® or PARI nebulizers; ear delivery; topical bath irrigation; topical spray application; topical irrigation application; topical gauze application; or other topical external application. For example, various embodiments comprising a topical treatment solution format including cefixime and/or nitrofurantoin may be administered via nasal irrigation delivery, nasal delivery, ear delivery, bath irrigation, topical spray, gauze, or topical irrigation. A bath irrigation may include submerging an infected tissue surface or irrigating the infected tissue surface. In one embodiment, a bath irrigation may be administered in a footbath, which may include a hand bath or soaking container, to treat or prevent an infection. The method may include adding the topical composition to a footbath. In some embodiments, the method may include addition of a carrier comprising an aqueous diluent. The aqueous diluent may be in addition to the carrier as described herein or may be the carrier. For example, a topical composition comprising a solution, cream, ointment, powder, gel, paste, or lotion format may be added to a footbath. Additional carrier comprising an aqueous diluent may also be added. In some embodiments, the topical composition prior to addition of the diluent comprises a concentrated topical composition, and following addition of the carrier comprising the diluent, the topical composition comprises the percent compositions or weight described herein. The footbath solution may be agitated and/or heated in some embodiments. A foot, hand, or other infected tissue surface may contact the footbath solution in the footbath for administration of the topical composition. In one aspect, cefixime and/or nitrofurantoin may be combined with a carrier comprising a diluent wherein all or a portion of the diluent may be selected from water, sodium chloride, saline, Dakin's solution, sodium hypochlorite, or combination thereof. In one example, the diluent comprises sterile water for irrigation. Such a composition may be administered to infected or wounded tissue such as skin, oral cavity, nasal cavity, respiratory system, anus, vagina, ear canal, hands, or feet.

In some examples, the topical composition comprises a treatment solution including cefixime and/or nitrofurantoin, such as powder from one or more cefixime and/or nitrofurantoin capsules, in an amount described herein without an additional antimicrobial pharmaceutical drug. For example, cefixime and/or nitrofurantoin capsule powder may be combined with a carrier or diluent to formulate a treatment solution format for nasal irrigation; topical bath irrigation, e.g., submersion; topical spray application; topical irrigation application; topical gauze application, or other topical external application, such as those described herein. The carrier or diluent may comprise an aqueous solution, non-aqueous solution, sodium hypochlorite, Dakin's solution, water, sterile water, water for injection, water for irrigation, hydrogen peroxide, or sodium chloride, for example. In some embodiments, cefixime and/or nitrofurantoin is combined with a suitable amount of carrier diluent to obtain a daily dosage of cefixime and/or nitrofurantoin, typically 1 to 2 administration volumes; however, additional administration volumes may be used. The administration volumes may be as disclosed herein.

In various embodiments, the topical composition including cefixime and/or nitrofurantoin is formulated for suppository administration at a body orifice, such as the rectum, vagina, or urethra. In some embodiments, the composition may comprise a dosage form including a capsule, tablet, gum, lozenge, or pouch configured for sublingual or sublabial administration. The body cavities or orifices may comprise one or more of the nasal cavity, nostrils, tear duct, anus, vagina, urethra, mouth, and ear canal.

The topical composition including cefixime and/or nitrofurantoin may be provided in an oral rinse solution or oral lozenge. The oral rinse may comprise a mouthwash. Oral administration may also include application or an ointment, lotion, cream, or gel.

The topical composition comprising cefixime and/or nitrofurantoin may be utilized to treat infections of the lower or upper respiratory tract. The topical composition may be prepared for intranasal administration such as a nasal solution, which may include a suspension or dispersion. The solution may be sprayed, inhaled, nebulized, or administered via liquid stream lavage or nasal irrigation. Administration may be to the sinus cavity or the lungs. In various embodiments, other active agents may be added for purposes of alleviating other undesirable conditions associated with an administration such as anesthetics, analgesics, anti-inflammatories, antibacterial agents, antiviral agents and emollients. In one example, a mucolytic agent may be added. Mucolytics are used to dissolve or breakdown mucus in the respiratory tract. In one example, the topical composition may include a mucolytic agent selected from the group consisting of acetylcysteine, erdosteine, bromheksin, carbocisteine and guaifenesin or pharmaceutically acceptable salts thereof. Excipients may be selected to assist in the release, dispersion, solubility, or the delivery of one or more of the active agents at the administration or target site, e.g., skin, lungs, respiratory surfaces, or one or more body orifices. For example, excipients may include synthetic or naturally derived excipients such as one or more of a base, solvent, surfactant, permeation enhancer, emollient, humectant, disintegrate, acid, base, pH modifying agent or buffer, solubility enhancer, or a carrier molecule or complex configured to enhance or modulate diffusion, localization, targeting, active or passive transport, or uptake, for example, of one or more active agents. Other pharmaceutically acceptable excipients or additives may include, for example, solvents, preservatives, flavorings, stabilizers (including antioxidants), colorants, lubricant, sorbent, glident, filler, bulking agent, and other additives used in preparations administered topically to skin, into the oral cavity, intranasally, or ear, or via the anus or vagina.

A nebulization format of the topical composition may comprise a dosage quantity of active agent within a suitable volume of carrier. In various embodiments, the suitable volume is that which is suitable for administration of the composition via nebulization. In one embodiment, the suitable volume is that which is suitable for administration via in a small volume nebulizer, which may be an intranasal nebulizer. In another embodiment, a suitable volume is that which is suitable for nasal irrigation. Intranasal administration via nebulization of the topical composition may efficiently deliver the nebulized composition to the respiratory tract, e.g., the nasal and paranasal sinus cavities. Once delivered, deposits of the active agents cefixime and/or nitrofurantoin, which may be in a concentrated state, may form on surfaces of the respiratory tract. Nebulization may be by any suitable commercially available nebulizer device, preferably an intranasal nebulizer. The active agents, such the cefixime and/or nitrofurantoin, may be mixed with the carrier to produce a nebulizer solution, which may include a suspension/dispersion, dosage form for small particle nebulization using a small particle nebulization delivery system. For example, the nebulizer solution dosage form may be formulated for inhalational delivery to the lungs via a small particle size nebulizer, such as a PARI or Sinustar™, Omron, or other nebulizer configured to nebulize the dosage form to produce particles or droplets less than 10 microns in size thereby allowing penetration into the lower respiratory tract, e.g., the lungs. In one embodiment, administration may comprise small particles or droplets, e.g., having aerosol characteristics, wherein the majority of the particles or droplets formed by the nebulization are less than 5 microns. In some embodiments, 60%, 70%, 80%, or greater of the particles or droplets are less than 5 microns. In various embodiments, nebulization with a small particle nebulizer produces nebulized aerosol particles wherein the majority of particles are less than 10 microns, 8 microns, 5 microns, or 3 microns. In these or other embodiments, the nebulized particles may be produced within a particle size dispersion wherein at least 50%, 60%, 70%, 80%, 90%, or 95% of the particles may be within about 3 microns and about 10 microns, about 3 microns and about 8 microns, about 3 microns and about 5 microns, about 5 microns and about 8 microns, about 5 microns and about 10 microns, or about 8 microns and about 10 microns. In some embodiments, the nebulized small particles may be inhaled into the upper airway and deposit thereafter at the paranasal sinus and nasal mucosa. In another embodiment, administration may include nebulization via a large particle nebulizer, which may include intranasal administration. Administration via large particle nebulization may include particles or droplets wherein a majority of such particles or droplets are larger than about 5 microns, about 10 microns, about 15 microns, about 20 microns or more, such as about 23 microns. In these or other embodiments, the nebulized particles may be produced within a particle size dispersion wherein at least 50%, 60%, 70%, 80%, 90%, or 95% of the particles may be within about 10 microns and about 25 microns, about 10 microns and about 20 microns, about 10 microns and about 15 microns, about 15 microns and about 25 microns, about 15 microns and about 20 microns, or about 20 microns and about 25 microns. In various embodiments, nebulized large particles may be inhaled intranasally into the nasal and paranasal sinus cavities for deposition on the frontal recess/sinus, spheno-ethmoid recess, ethmoid cavity, sphenoid and maxillary sinuses, turbinates, middle meatus, and olfactory cleft. Large particle nebulization may utilize the active agents in a low volume base to ensure high concentrations of actives remain in the nasal cavity or deposit on respiratory surfaces in high concentration droplets. In one embodiment, large particle nebulization is used to deliver an administration volume of between about 0.2 mL to about 15 mL for retention in the nasal and paranasal sinus cavities.

The topical composition comprising cefixime and/or nitrofurantoin may also be utilized to treat an infection of the ear and be administered to the same. For example, the topical composition may be utilized for aural administration by instillation of a treatment solution into the ear canal.

As introduced above, the method of formulating the topical composition may include combining active agents in addition to the antimicrobial agent e.g., cefixime and/or nitrofurantoin. In some embodiments, the additional active agent comprises one or more active agents selected from an anti-inflammatory agent, a steroid agent, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof.

It will be appreciated that topical compositions herein may include or specifically exclude an additional active agent. It will also be appreciated that topical compositions may exclude an antimicrobial agent and rather include one or more of the additional active agents described herein.

The method of formulating the topical composition comprising additional active agents may include combining all or a portion of an additional active agent from a powder format, e.g., from bulk powder, crushed tablet, injection powder, or other commercially available composition. In various embodiments, such additional active agents may be combined with the carrier together with or separate from all or a portion of the antimicrobial agent powder or other format. According to a method, all or a portion of an additional active agent may be provided in a format selected from a solution, emulsion, gel, cream, lotion, ointment, or other format and may be combined with the carrier together with or separate of all or a portion of the antimicrobial agent.

In one example, all or a portion of the additional active agent may be mixed with all or a portion of the antimicrobial agent prior to being added to a carrier. In another example, the antimicrobial agent is added to the additional active agent that is provided in a commercially available medicated composition comprising the carrier. In another example, the antimicrobial agent comprises a commercially available medicated composition comprising all or a portion of the carrier to which the additional active agent is combined. In another example, the antimicrobial agent comprises a commercially available medicated composition comprising a portion of the carrier and the additional active agent comprises another portion of the carrier. In one embodiment, any of the above formulations may include addition of carrier or components thereof that are not commercially available medicated compositions such as commercially available bases, liquid carriers/vehicles such as aqueous and non-aqueous liquids, powders, or components thereof, such as those identified herein.

In one embodiment, formulating the topical composition comprises combining the antimicrobial agent with a commercially available medicated composition comprising all or a portion of the additional active agent.

In one embodiment, the method of formulating the topical composition comprises combining an antimicrobial agent and a nonsteroidal anti-inflammatory drug (NSAID) agent. In some examples, the method may also include combining a carrier. The NSAID agent may include one or more NSAIDS selected from oxicams, such as meloxicam or piroxicam; salicylic acid derivatives, such as aspirin, diflunisal, salsalate, or trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, or tolmetin; fenamates, such as meclofenamate; and/or COX-2 inhibitors, such as celecoxib, rofecoxib, or valdecoxib. In various embodiments, the topical composition may comprise between approximately 0.01% and approximately 20% by weight NSAID agent.

In one embodiment, the method of formulating the topical composition comprises combining the antimicrobial agent, an NSAID agent identified herein, and a carrier in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the NSAID agent in an amount between approximately 0.01% and approximately 20% by weight, such as between approximately 2% and approximately 10% or any other percent, percent range, or percent therebetween by weight described herein. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, or combination thereof. Combining the NSAID may comprise adding a bulk powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial or an additional active agent as described herein. In one example, the carrier includes all or a portion of the NSAID agent and includes a commercially available medicated NSAID composition comprising a cream, ointment, suspension, lotion, gel, or solution. For example, the carrier may comprise a commercially available medicated NSAID composition comprising a Diclofenac Sodium Solution. Diclofenac Sodium Solution may contain, for example, 1.5% (w/w), diclofenac sodium wherein each 1 mL of solution contains approximately 16.05 mg of diclofenac sodium. In one embodiment, the diclofenac solution comprises a diclofenac sodium solution, 1.5% (w/w), such as that which is manufactured under the trade name PENNSAID® by Nuvo Manufacturing, Varennes, Quebec, Canada or Diclofenac Sodium Topical Solution, 1.5% (w/w), manufactured by Apotex Inc. Toronto, Ontario, Canada M9L 1T9 for Apotex Corp. Weston, Fla. 33326 for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used.

In one embodiment, the method of formulating the topical composition comprises combining an antimicrobial agent and a local anesthetic agent. In some examples, the method may also include combining a carrier. The local anesthetic agent may be selected from lidocaine, prilocaine, benzocaine, or combination thereof. The local anesthetic agent may comprise between approximately 0.01% and approximately 15% by weight of the topical composition.

In one embodiment, the method of formulating the topical composition comprises combining the antimicrobial agent and a local anesthetic agent identified herein in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the local anesthetic agent in an amount between approximately 0.01% and approximately 12% by weight, such as between approximately 2% and approximately 10% or any other percent, percent range, or percent therebetween by weight described herein. In some examples, the method may also include combining a carrier. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, cefixime, tetracycline, nitrofurantoin, or combination thereof. Combining the local anesthetic may comprise adding a bulk powder, capsule powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the local anesthetic agent and includes a commercially available medicated local anesthetic composition comprising a cream, ointment, suspension, lotion, gel, or solution. For example, the carrier may comprise a commercially available medicated Lidocaine Ointment, Lidocaine Cream, Lidocaine and Prilocaine Cream, or Lidocaine Solution. In one instance, a method of making the topical composition comprises combining the antimicrobial agent with a Lidocaine Solution including lidocaine in an aqueous solution. The lidocaine solution may be a commercially available lidocaine topical solution, such as lidocaine hydrochloride solution for topical administration. The carrier may comprise the lidocaine solution. The lidocaine hydrochloride solution may contain, for example, 4% lidocaine (w/v) wherein each mL includes 40 mg lidocaine HCl. For example, in one embodiment, the lidocaine topical solution may be Lidocaine Hydrochloride Topical Solution USP, 4% manufactured by IGI Labs, Inc., Buena, N.J., in 50 mL screw cap glass bottles. The lidocaine hydrochloride topical solution may contain various inactive ingredients such as methylparaben, purified water, and sodium hydroxide to adjust pH to 6.0-7.0.

In one embodiment, the method of formulating the topical composition comprises combining an antimicrobial agent, e.g., cefixime and/or nitrofurantoin, and a steroid agent. In some examples, the method may also include combining a carrier. In one example, the steroid agent comprises a corticosteroid selected from amcinonide, betamethasone dipropionate, betamethasone valerate, clobetasol propionate, desoximetasone, diflorasone diacetate, flurandrenolide, fluticasone propionate, fluocinonide, halcinonide, halobetasol propionate, mometasone furoate, triamcinolone acetonide, or combination thereof. In another example, the steroid agent comprises a corticosteroid selected from betamethasone dipropionate, betamethasone valerate, clobetasol propionate, fluticasone propionate, fluocinonide, halcinonide, halobetasol propionate, or combination thereof. In various embodiments, the topical composition comprises between approximately 0.001% and approximately 1% by weight steroid agent.

In one embodiment, the method of formulating the topical composition comprises combining the antimicrobial agent, e.g., cefixime and/or nitrofurantoin, and a steroid agent identified herein in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the steroid agent in an amount between approximately 0.01% and approximately 2% by weight, such as between approximately 0.05% and approximately 1% or any other percent, percent range, or percent therebetween by weight described herein. In some examples, the method may also include combining a carrier. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, cefixime, tetracycline, nitrofurantoin, or combination thereof. Combining the steroid agent may comprise adding a bulk powder, capsule powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the steroid agent and includes a commercially available medicated steroid composition comprising a cream, ointment, suspension, lotion, gel, or solution. For example, the carrier may comprise a commercially available Clobetasol Propionate Cream, Foam, Gel, or Ointment, Diflorasone Diacetate Cream or Ointment, Amcinonide Cream, Lotion, or Ointment, Betamethasone Dipropionate Cream, Lotion, Gel, or Ointment, Desoximetasone Cream or Ointment, Fluocinonide Cream, Fluocinonide Cream, Ointment, or Gel, Halcinonide Cream or Ointment, Fluocinolone Acetonide Cream, Ointment, Oil, or Solution, Halcinonide Cream or Ointment, Betamethasone Valerate Cream, Lotion, or Ointment, Diflorasone Diacetate Cream or Ointment, Triamcinolone Acetonide Cream or Ointment, Halobetasol Propionate Cream, Lotion, or Ointment, Desoximetasone Cream, Gel, or Ointment, Mometasone Furoate Cream or Ointment, Fluticasone Propionate Cream, Flurandrenolide Cream, Lotion, or Ointment, or combination thereof. In another example, the corticosteroid topical composition is selected from Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Fluocinolone Acetonide Cream, Ointment, Oil, or Solution, Halcinonide Cream or Ointment, Triamcinolone Acetonide Cream or Ointment, Halobetasol Propionate Cream or Ointment, Mometasone Furoate Cream or Ointment, Flurandrenolide Cream or Ointment, or combination thereof. In still another example, the carrier comprises Clobetasol Propionate Cream or Ointment, Fluocinonide Cream or Ointment, Fluocinolone Acetonide Cream, Ointment, Oil, or Solution, Halcinonide Cream or Ointment, Halobetasol Propionate Cream, or Desoximetasone Cream or Ointment, Triamcinolone Acetonide Cream or Ointment, Betamethasone Dipropionate Cream or Ointment, or combination thereof. In another example, the carrier comprises Clobetasol Propionate Cream, Foam, Gel, or Ointment, 0.05%, Diflorasone Diacetate Cream or Ointment, 0.05%, Amcinonide Cream, Lotion, or Ointment, 0.1%, Betamethasone Dipropionate Cream, Lotion, Gel, or Ointment 0.05%, Desoximetasone Cream or Ointment 0.25%, Fluocinonide Cream 0.1%, Fluocinonide Cream, Ointment, or Gel, 0.05%, Fluocinolone Acetonide Cream 0.01%, Fluocinolone Acetonide Cream 0.025%, Fluocinolone Acetonide Oil 0.01%, Fluocinolone Acetonide Ointment 0.01%, Fluocinolone Acetonide Ointment 0.025%, Fluocinolone Acetonide Solution 0.01%, Halcinonide Cream or Ointment, 0.1%, Betamethasone Valerate Cream, Lotion, or Ointment 0.1%, Diflorasone Diacetate Cream or Ointment, 0.05%, Triamcinolone Acetonide Cream or Ointment, 0.1%, Triamcinolone Acetonide Ointment, 0.05%, Halobetasol Propionate Cream, Lotion, or Ointment, 0.05%, Desoximetasone Cream, Gel, or Ointment 0.05%, Mometasone Furoate Cream or Ointment, 0.1%, Fluticasone Propionate Cream, 0.05%, Flurandrenolide Cream, Lotion, or Ointment, 0.05%, or combination thereof. In still a further example of the above, the corticosteroid topical composition is selected from Clobetasol Propionate Cream or Ointment, 0.05%, Diflorasone Diacetate Cream or Ointment, 0.05%, Amcinonide Cream or Ointment, 0.1%, Betamethasone Dipropionate Cream or Ointment 0.05%, Desoximetasone Cream or Ointment 0.25%, Fluocinonide Cream 0.1%, Fluocinonide Cream or Ointment, 0.05%, Fluocinolone Acetonide Cream 0.01%, Fluocinolone Acetonide Cream 0.025%, Fluocinolone Acetonide Oil 0.01%, Fluocinolone Acetonide Ointment 0.01%, Fluocinolone Acetonide Ointment 0.025%, Fluocinolone Acetonide Solution 0.01%, Halcinonide Cream or Ointment, 0.1%, Diflorasone Diacetate Cream or Ointment, 0.05%, Triamcinolone Acetonide Cream, 0.1%, Halobetasol Propionate Cream or Ointment, 0.05%, Desoximetasone Cream or Ointment 0.05%, Mometasone Furoate Cream or Ointment, 0.1%, or Flurandrenolide Cream or Ointment, 0.05%, or combination thereof. In still a further embodiment, the corticosteroid topical composition is selected from Betamethasone Dipropionate Cream or Ointment 0.05%, Clobetasol Propionate Cream or Ointment, 0.05%, Desoximetasone Cream or Ointment 0.25%, Fluocinonide Cream 0.1%, Fluocinonide Cream or Ointment, 0.05%, Fluocinolone Acetonide Cream 0.01%, Fluocinolone Acetonide Cream 0.025%, Fluocinolone Acetonide Oil 0.011%, Fluocinolone Acetonide Ointment 0.01%, Fluocinolone Acetonide Ointment 0.025%, Fluocinolone Acetonide Solution 0.01%, Triamcinolone Acetonide Cream, 0.1%, Halobetasol Propionate Cream, 0.05%, or Desoximetasone Cream or Ointment 0.05%, or combination thereof.

In one embodiment, the method of formulating the topical composition comprises combining an antimicrobial agent, e.g., cefixime and/or nitrofurantoin, and an additional active agent selected from one or more muscle relaxants, anticonvulsants, nerve depressants, NMDA receptor antagonists, opiates, opioid agonists, or combinations thereof. In some examples, the method may also include combining a carrier. A muscle relaxant agent may comprise between approximately 0.001% and approximately 5% by weight of the topical composition and be selected from baclofen, carisoprodol, chlorzoxazone, cyclobenzaprine, dantrolene, diazepam, metaxalone, methocarbamol, orphenadrine, quinine sulfate, tizanidine, or combination thereof; an anticonvulsant or nerve depressant agent may comprise between approximately 0.01% and approximately 20% by weight of the topical composition and be selected from gabapentin, topiramate, lamotrigine, or combinations thereof; a NMDA receptor antagonist agent may include ketamine; an opiate or opioid agonist agent may include tramadol, oxycodone, morphine, methadone, hydromorphone, fentanyl, hydrocodone, codeine, propoxyphene, butalbital, pentazocine, or combination thereof. The antimicrobial agent may be combined in an amount between approximately 0.01% and approximately 10% by weight of the topical composition, such as between approximately 0.5% and approximately 5% or any other percent, percent range, or percent therebetween by weight described herein. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, cefixime, tetracycline, nitrofurantoin, or combination thereof. Combining the additional active agent may comprise adding a bulk powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the additional active agent and includes a commercially available medicated composition comprising the additional active agent in a cream, ointment, suspension, lotion, gel, or solution.

In one embodiment, the method of formulating the topical composition comprises combining an antimicrobial agent, e.g., cefixime and/or nitrofurantoin, and a keratolytic agent. In some examples, the method may also include combining a carrier. The keratolytic agent selected form urea, salicylic acid, papain, or combinations thereof. For example, the topical composition may comprise the antimicrobial agent and urea. In various embodiments, the topical composition may comprise between approximately 1% and approximately 30% by weight urea.

In one embodiment, the method of formulating the topical composition comprises combining the antimicrobial agent, e.g., cefixime and/or nitrofurantoin, and a keratolytic agent identified herein in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the keratolytic agent in an amount between approximately 5% and approximately 30% by weight, such as between approximately 10% and approximately 20% or any other percent, percent range, or percent therebetween by weight described herein. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, cefixime, tetracycline, nitrofurantoin, or combination thereof. Combining the keratolytic may comprise adding a bulk powder, crushed tablet, e.g., crushed urea tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the keratolytic agent and includes a commercially available medicated keratolytic comprising a urea ointment or cream. For example, the carrier may comprise REA LO 40®, which is a 40.0% urea cream. Each gram of REA LO 40® contains 400 mg urea as the active ingredient and the following inactive ingredients: purified water, emulsifying wax, glycerin, isopropyl myristate, sorbitol, neopentyl glycol dicaprylate/dicaprate, tridecyl stearate, tridecyl trimellitate and dimethyl isosorbide. The urea cream may comprise various percentages of urea by weight (prior to compounding or prior to combination with another carrier), such as 10%, 15%, 20%, 25%, 30%, 35%, 40%, or any other commercially available percentage by weight. In various embodiments, the urea cream may be Urix 40 Urea Cream marketed by Topix Pharmaceuticals, Inc. Urix 40 Urea Cream includes 40% urea or 400 mg urea per gram and further includes Carbomer, Cyclomethicone, Dimethicone Silyate, Dimethiconol, Glycerin, Hydrogenated Lecithin, Imidazolidinyl Urea, Petrolatum, Phenyl Trimethicone, Polyphosphorylcholine Glycol Acrylate, Triethanolamine, Water, and Xanthan Gum. In additional embodiments, the urea cream may be Rea Lo 40 topical or Rea Lo 30 topical marketed by Crown Laboratories. Rea Lo 40 topical comprises 400 mg urea per gram and Rea Lo 30 topical comprises 300 mg urea per gram. Rea Lo 40 topical and Rea Lo 30 topical further include purified water, emulsifying wax, glycerin, isopropyl myristate, sorbitol, neopentyl, glycol dicaprylate/dicaprate, tridecyl stearate, tridecyl trimellitate and dimethyl isosorbide. In additional embodiments, the urea cream may be Urea 10% Cream by Stratus Pharmaceuticals, Inc. Urea 10% Cream includes 10% urea or 100 mg urea per gram, and further includes Carbomer, Fragrance, Isopropyl Myristate, Isopropyl Palmitate, Propylene Glycol, Purified Water, Sodium Laureth Sulfate, Stearic Acid, Trolamine and Xanthan Gum. It is to be understood that the above urea creams (or any other urea cream) may be diluted or cut prior to or, in some embodiments, after compounding or otherwise combining the urea cream with additional creams and/or actives. Thus, the topical composition may comprise less urea by weight than was present in the urea cream prior to compounding or combination with another cream and/or active.

The method of formulating a topical composition may comprise combining an antimicrobial agent comprising crushed oral tablets and a carrier. In one example, the antimicrobial agent comprises an antifungal component comprising voriconazole and the method of formulating the topical composition comprises addition of a crushed voriconazole tablet to a carrier. The voriconazole tablets may comprise commercially available voriconazole 50 mg, 100 mg, 200 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% voriconazole by weight. To formulate a topical composition comprising a desired percent by weight voriconazole, the total desired weight of the topical composition is subtracted from the weight of crushed oral voriconazole tablet powder needed to obtain the desired percent by weight voriconazole. The weight of voriconazole tablet powder needed is determined by multiplying the weight of active needed to obtain the desired percent by weight voriconazole in the topical composition. For example, a topical composition comprising 1% voriconazole may be formulated combining powder obtained from 200 mg oral voriconazole tablets. The weight of voriconazole tablet powder needed is determined by multiplying the weight of voriconazole needed to obtain the desired percent by weight voriconazole in the topical composition. Here, a 1% voriconazole composition includes 10 mg voriconazole per gram. If a 200 mg voriconazole tablet weights approximately 450 mg, 22.5 mg of crushed voriconazole tablet powder comprises 10 mg voriconazole. Therefore, 22.5 mg of crushed voriconazole tablet powder is combined for each gram of topical composition. Consequently, 977.5 mg of carrier, and additional active agents, if any, may be combined with 22.5 mg of crushed voriconazole tablet powder to formulate each gram of topical composition to formulate a 1% by weight topical composition. Other percent compositions may be formulated as described herein. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antifungal component comprising fluconazole and the method of formulating the topical composition comprises addition of a crushed fluconazole tablet to a carrier. The fluconazole tablets may comprise commercially available fluconazole 100 mg and/or 200 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% fluconazole by weight. To formulate a topical composition comprising a desired percent by weight fluconazole, the total desired weight of the topical composition is subtracted from the weight of crushed oral fluconazole tablet powder needed to obtain the desired percent by weight fluconazole in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antibacterial component comprising linezolid and the method of formulating the topical composition comprises addition of a crushed linezolid tablet to a carrier. The linezolid tablets may comprise commercially available linezolid 600 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% linezolid by weight. To formulate a topical composition comprising a desired percent by weight linezolid, the total desired weight of the topical composition is subtracted from the weight of crushed oral linezolid tablet powder needed to obtain the desired percent by weight linezolid in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antibacterial component comprising levofloxacin and the method of formulating the topical composition comprises addition of a crushed levofloxacin tablet to a carrier. The levofloxacin tablets may comprise commercially available levofloxacin 250 mg, 500 mg, 750 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% levofloxacin by weight. Other embodiments may include commercially available levofloxacin bulk powder, levofloxacin oral solution, levofloxacin for injection, or a combination thereof, instead of or together with levofloxacin crushed tablets. To formulate a topical composition comprising a desired percent by weight levofloxacin, the total desired weight of the topical composition is subtracted from the weight of crushed oral levofloxacin tablet powder needed to obtain the desired percent by weight levofloxacin in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antibacterial component comprising ciprofloxacin and the method of formulating the topical composition comprises addition of a crushed ciprofloxacin tablet to a carrier. The ciprofloxacin tablets may comprise commercially available ciprofloxacin 250 mg, 500 mg, 750 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% ciprofloxacin by weight. To formulate a topical composition comprising a desired percent by weight ciprofloxacin, the total desired weight of the topical composition is subtracted from the weight of crushed oral ciprofloxacin tablet powder needed to obtain the desired percent by weight ciprofloxacin in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

According to a method of formulating the topical composition, wherein the topical composition comprises a cream, the method may include combining the antimicrobial agent, e.g., cefixime and/or nitrofurantoin, and a carrier to formulate a cream. The carrier may comprise a cream base, thickening agent, solvent, diluent, for example. In one example, the method includes combining a commercial medicated solution comprising all or a portion of the antimicrobial agent and a carrier comprising a base cream or thickening agent. In another embodiment, the method includes combining a commercially available medicated cream comprising all or a portion of the antimicrobial agent with an additional active agent. In another embodiment, the method includes combining a commercially available medicated cream comprising a portion of the antimicrobial agent with a commercially medicated cream comprising another portion of the antimicrobial agent. In another embodiment, the method includes combining a commercially available medicated cream comprising all or a portion of the antimicrobial agent or an additional active agent with a commercially available medicated cream, ointment, solution, or powder comprising all or a portion of the antimicrobial agent or an additional active agent. Additional carrier components may also be added. In one example, the method includes combining an excipient base powder comprising a blend of micronized xylitol and poloxamers to make a homogeneous compounded composition. The combined ingredients may me mixed to form a smooth cream.

In an aspect, a treatment solution comprising levofloxacin as described herein may be topically administered to an outer body region. The outer body region may include an outer body surface such as skin or adjoining tissues, which in some instances may be exposed through broken skin. The outer body surface may be infected or be suspected of being infected. In one example, the treatment solution may be topically administered to a skin area by contacting a skin area that is or is suspected to be infected by a bacterium or fungus. Contacting may include bathing, e.g., submerging or irrigating, the skin area. The treatment solution may be contacted to damaged or undamaged skin. For example, the treatment solution may contact broken skin, underlying tissue, or both to bath the wounded area. Topical administration may include a bathing administration, which may include submerging all or a portion of an outer body region or surface in the treatment solution, e.g., in a bath application or by irrigating all or a portion of the outer body region, or otherwise contacting all or a portion of the outer body region or surface, such as by spraying, with the treatment solution in a spray application. The outer body region may comprise skin such as a skin surface a foot, hand, appendage, trunk, or portion thereof. The treatment solution may be topically administered, outside the body, from the external side of the body, to an affected body surface or underlying tissue. For example, a foot, hand, or other body region may be placed in a bathing container or otherwise contacted with the treatment solution in the bathing container for a suitable amount of time, e.g., 10 minutes or so, which may be repeated twice daily.

Methods of Treating or Preventing an Infection or Wound

The present disclosure also describes methods of treating an infection or wound by providing or administering a topical composition described herein. In some embodiments, the method may include formulating the topical composition for topical treatment of an infection or wound. The treatment method may include contacting the topical composition to skin, nails, or body orifice that is infected or believed to be infected. The infection may be of an exterior surface of the body, an orifice, or internal. Administration may include bath-irrigation, topical irrigation via a syringe, administration in a topical powder, or a topical gel, cream, ointment, or lotion. Administration may be to an external surface of the body or to anal or vaginal surfaces. In various embodiments, the topical composition may be administered via contact to an infected area such as to skin of a head, face, ears, nose, neck, shoulder, torso, chest, stomach, waistline, extremity, arm, hand, finger, nail, groin, buttock, leg, foot, or toe, for example. In an embodiment of a method to treat an internal infection, the topical composition may be administered topically as described herein wherein one or more active agents are transdermally delivered locally or for systemic circulation. Additional active agents may be utilized in the topical composition to reduce pain, irritation, and inflammation such as NSAIDs, steroids, local anesthetics, anticonvulsants, antidepressants, for example. In various embodiments, the topical composition may be administered 1 to 2 times daily or as otherwise needed.

In one embodiment, a topical composition may be used to treat an infection or suspected infection accompanying a hyperkeratotic skin conditions that are marked by a thickening of the outer layers of skin. Methods of using the topical composition may include treating an individual in need by topically applying the composition to affected skin. Conditions treated may include conditions such as those marked by thickening of the skin, referred to as hyperkeratosis. The compounded topical composition described herein may thus be applied to such affected areas of the skin to treat the affected area. The composition may alleviate symptoms such as redness, swelling, or itching. The composition may accelerate the healing process with respect to the affected skin. In various embodiments, the topical composition may be administered to treat hyperkeratotic conditions. The hyperkeratotic skin condition treated may include chronic eczema, corns, calluses, warts, seborrheic keratosis, lichen planus, actinic keratosis, as examples. The hyperkeratotic skin conditions may be caused by irritation, such as physical pressure or rubbing, chemical, infection, sunlight or radiation, or inherited conditions, for example. In an embodiment, the topical composition may be administered to such affected skin in a preventative treatment regime to combat proliferation of microbial infections with respect to the thickened skin layers. In some such embodiments, the topical composition may include a keratolytic agent as described herein.

Topical compositions comprising cream, lotion, paste, ointment, and similar formats may be applied by contact to skin, or mucosal tissue with respect to anal or vaginal administration. In some embodiments, the topical composition may be formulated in a shampoo carrier for administration in a shampoo. In some formats, the composition may be administered to an infected or target area via spray, drops, wash, swab, sponge, absorbent dressing, coating (e.g., a nail lacquer), soaking, submerging, footbath, instillation or irrigation. Embodiments comprising a nail lacquer formulation may be applied directly to nails, to treat a bacterial or fungal nail infection.

Various embodiments comprising a solution format may be administered in a footbath, which may include a hand bath or soak, to treat or prevent an infection. The method may include adding the topical composition to a footbath. In some embodiments, the method may include addition of a carrier comprising an aqueous diluent. The aqueous diluent may be in addition to the carrier as described herein or may be the carrier. For example, a topical composition comprising a solution, cream, ointment, powder, gel, paste, or lotion format may be added to a footbath. Additional carrier comprising an aqueous diluent may also be added. In some embodiments, the topical composition prior to addition of the diluent comprises a concentrated topical composition, and following addition of the carrier comprising the diluent, the topical composition comprises the percent compositions described herein. The footbath solution may be agitated and/or heated in some embodiments. A foot or a hand may contact the footbath solution in the footbath for administration of the topical composition.

A footbath refers to a container that can hold some volume (e.g., approximately 1.0 liters to approximately 30 liters) of a treatment or footbath solution, which may typically be an aqueous solution or suspension, and is designed to physically accommodate at least a portion of one or both feet of a subject. A footbath administration includes administration of the topical composition utilizing a footbath. A footbath may be used as a hand bath; however, smaller bathing containers may typically be utilized as hand baths. In various embodiments, footbath solutions may be utilized as hand bath solutions. A footbath may also be utilized for other body portions other than the hand or foot, e.g., legs, arms, limbs, torso, scalp, ear, face, chest, or back. A footbath can comprise several features or agents that effect various functions. For example, a footbath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or other body portion of the subject within the bath, a massage agent (e.g., a roller) that provides massaging contact to at least a portion of one or both feet, a pedicure agent that can clean or contact a foot or feet with a pumice, or a combination thereof. In an aspect, a footbath can have a waterfall element. In an aspect, an agitation agent or an agitator can be coupled to both a motor and the footbath. In an aspect, a footbath can comprise one or more splashguards and other spill-resistant features to ensure that the water remains enclosed within a container. A footbath may also accommodate a subject's calves, meaning that the container is "deep" so as to allow the enclosed water to contact both the feet and at least a portion of the calves of the subject. Several manufacturers market footbaths including PIBB, Dr. Scholl's, Kendal, Conair (e.g., Model FB5X, FB3, FB27R, FB30, FB52, etc.), and Brookstone.

A method of treating or preventing an infection may include formulating a footbath solution comprising combining the antimicrobial agent and a carrier comprising a diluent. The carrier may comprise a liquid or dry powder diluent, base powder, cream, ointment, or other carrier identified herein.

A method treating or preventing an infection may include formulating an irrigation solution comprising combining the antimicrobial agent and a carrier comprising a diluent. The carrier may comprise a liquid or dry powder diluent, base powder, cream, ointment, or other carrier identified herein.

A method of treating a wound may include formulating a wound ointment, powder, cream, or solution comprising combining the antimicrobial agent and a carrier. The carrier may comprise a liquid or dry powder diluent, base powder, cream, ointment, or other carrier identified herein.

Formulating a topical composition comprising a solution for a footbath, irrigation, or spray may comprise adding the antimicrobial agent to a carrier comprising a diluent and agitating or mixing. The topical composition may be administered in a footbath by contacting a skin surface that is infected or suspected to be infected. The skin surface may be a hand, foot, limb, torso, or other surface identified herein. The topical composition may be administered in by irrigation by pouring onto skin or an orifice. In some embodiments, the skin or mucosal tissue comprises a wound, which may include broken or unbroken tissue.

In various embodiments, the diluent may comprise an aqueous solution, non-aqueous solution, sodium hypochlorite, hydrogen peroxide, Dakin's solution, or sodium chloride. In an aspect, the amount of diluent can be approximately 3.75 mL to approximately 60 mL. In an aspect, the amount of diluent can be approximately 15 mL. In some embodiments, the amount of diluent may be between 0.5 L and 5 L, or more, such as sufficient diluent to achieve a desired volume, such as those identified elsewhere herein. In an aspect, the method can comprise adding to the diluent an excipient base powder comprising a blend of micronized xylitol and poloxamers. In an aspect, the excipient base powder can comprise LoxaSperse® excipient base powder. In an aspect, the excipient base powder can comprise LoxaSperse® excipient base powder and XyliFos® excipient base powder. In an aspect, an excipient base powder can be obtained from a bulk source.

In an aspect, the subject has been diagnosed with or is suspected of having a bacterial infection that affects exterior skin or mucosal tissue of the vaginal orifice or anus. In an aspect, the subject has been diagnosed with or is suspected of having a fungal infection exterior skin or mucosal tissue of the vaginal orifice or anus.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots, gloves, or clothing.

In some embodiments, a method of treating or preventing a, infection associated with a Candida, such as Candida albicans, Candida auris, Candida glabrata, Candida krusei, or Candida tropicalis may include topically applying the topical composition to target skin or mucosal surface. In some examples, the antimicrobial agent may comprise an antifungal component comprising an azole. In one example, the antifungal component comprises itraconazole. In a further example, the topical composition comprises itraconazole oral solution. In a further example, the topical composition comprises itraconazole oral solution and a carrier, such as a diluent or base for compounding. The topical composition may also include one or more additional antifungal active drugs, an antibacterial component, and/or one or more additional active agents.

In an aspect, contacting can comprise placing at least part of the skin or mucosal tissue of the subject believed to be infected or of which infection is to be prevented in the footbath. In an aspect, contacting can comprise placing at least part of one or both feet of the subject in the footbath for approximately 5 to approximately 15 minutes.

In one embodiment, the method may include heating the solution contained within the footbath. In an aspect, a footbath can comprise a mechanical agitation agent operable to mechanically agitate the enclosed solution, a heating agent to heat the enclosed solution, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the footbath. Motors and agitators are known to the art. In an aspect, mechanical agitation can serve to distribute the compounded composition throughout the water contained within the footbath. Heating agents and/or means to heat water in a compartment are known to the art.

In an embodiment, the topical composition comprises a nasal irrigation solution comprising a carrier selected from an aqueous solution, water, or saline. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

In an embodiment, the topical composition comprises a nebulization solution comprising a carrier selected from an aqueous solution, water, or saline. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

In an embodiment, the topical composition comprises a solution for aural administration comprising a carrier selected from an aqueous solution, water, or saline. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

In an embodiment, the topical composition comprises a bath or irrigation solution comprising a carrier selected from an aqueous solution, water, saline, hydrogen peroxide, or sodium hypochlorite. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

In an embodiment, the topical composition comprises a topical spray solution comprising a carrier selected from an aqueous solution, water, saline, hydrogen peroxide, or sodium hypochlorite. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

In an embodiment, the topical composition comprises a topical gauze solution comprising a carrier selected from an aqueous solution, water, saline, hydrogen peroxide, or sodium hypochlorite. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

In an embodiment, the topical composition comprises a nail lacquer solution or gel comprising a carrier selected from an aqueous solution, water, saline, hydrogen peroxide, or sodium hypochlorite. The topical composition may comprise nitrofurantoin in an amount between approximately 25 mg and approximately 200 mg in an administration volume. In another embodiment, the topical composition may comprise cefixime in an amount between approximately 200 mg and approximately 400 mg in an administration volume. The topical composition may usually be administered 1 to 2 times daily, but in some instances may also be administered 3 times daily. Additional actives and carrier components described herein may also be included.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

The term "contacting" as used herein refers to bringing one or more disclosed compositions, disclosed compounded compositions, or disclosed antimicrobial agents together with water and an intended target (such as at least a portion of one or both feet of a subject) or targeted area (such as an area diagnosed with, suspected of having a bacterial infection or a fungal infection, or susceptible to developing a bacterial infection or a fungal infection) in such a manner that the disclosed composition, a disclosed compounded composition, or a disclosed antimicrobial agent can exert an effect on the intended target or targeted area either directly or indirectly. In an aspect, "contacting" means to insert or immerse at least a portion of one or both feet of a subject into the water contained within a footbath.

The term "mixing" as used in a disclosed method of making a compounded composition, for example, means to physically combine the recited components so as to achieve a homogeneous compounded composition (which can be a dry powder formulation). For example, in an aspect, an antibacterial component and an antifungal component can be mixed with an excipient base powder; that is, an antibacterial component and an antifungal component are physically combined with an excipient base powder and shaken, or stirred, or agitated so as to achieve a homogeneous compounded composition. In an aspect, multiple recited components can be mixed together (i.e., antibacterial component, an antifungal component, an excipient base powder, and one or more additional antimicrobial agents (i.e., antibacterial component and antifungal component). In an aspect, "mixing" can also include sifting the homogeneous compounded composition though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogeneous compounded composition.

Also, in an aspect, "mixing" can be used to describe the process of making a solution by adding one or more of a disclosed compounded composition, a disclosed composition, or a disclosed antimicrobial agent to a diluent. For example, mixing means to physically combine one or more of a disclosed compounded composition, a disclosed composition, or a disclosed antimicrobial agent with a diluent.

"Mixing" can occur in a disclosed mixing container. In an aspect, a mixing container can have a pre-determined size that can measure or hold a pre-determined amount or volume. For example, in an aspect, a mixing container can measure or hold an amount of approximately 1 ounces to approximately 30 ounces. In an aspect, mixing container can measure or hold approximately 1 ounce, 2 ounces, 3 ounces, 4 ounces, 5 ounces, 6 ounces, 7 ounces, 8 ounces, 9 ounces, 10 ounces, 11 ounces, 12 ounces, 13 ounces, 14 ounces, 15 ounces, 16 ounces, 17 ounces, 18 ounces, 19 ounces, 20 ounces, 21 ounces, 22 ounces, 23 ounces, 24 ounces, 25 ounces, 26 ounces, 27 ounces, 28 ounces, 29 ounces, or 30 ounces. In an aspect, a mixing container can measure or hold approximately 6 ounces. In an aspect, a mixing container can measure or hold approximately 16 ounces.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient. A subject can have diabetes. A subject can be obese. A subject can have circulatory issues. A subject can have a bacterial infection, be suspected of having a bacterial infection, or be at risk of developing a bacterial infection. A subject can have a fungal infection, be suspected of having a fungal infection, or be at risk of developing a fungal infection. For example, a subject can have damaged or moist skin, can have chronic disease, or can be immunocompromised. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action, but which may also be encompassed by treating.

As used herein, the term "diagnosed" means having been subjected to a physical examination by a person of skill, for example, a physician, and found to have a condition that can be diagnosed or treated by the compounds, compositions, agents, or methods disclosed herein. For example, "diagnosed with a bacterial infection" means having been subjected to a physical examination by a person of skill, for example, a physician, and found to have a condition that can be diagnosed or can be treated by a disclosed compound or composition or agent that can prevent or inhibit a bacterial infection. For example, "suspected of having a bacterial infection" can mean having been subjected to a physical examination by a person of skill, for example, a physician, and found to have a condition that can be likely be diagnosed as or can likely be treated by a disclosed compound or composition or agent that can prevent or inhibit a bacterial infection, or it can mean that the subject believes that he or she has a bacterial infection. For example, "diagnosed with a fungal infection" means having been subjected to a physical examination by a person of skill, for example, a physician, and found to have a condition that can be diagnosed or can be treated by a disclosed compound or composition or agent that can prevent or inhibit a fungal infection. For example, "suspected of having a fungal infection" can mean having been subjected to a physical examination by a person of skill, for example, a physician, and found to have a condition that can be likely be diagnosed as or can likely be treated by a disclosed compound or composition or agent that can prevent or inhibit a fungal infection, or it can mean that the subject believes that he or she has a fungal infection.

As used herein, the terms "administering" and "administration" refer to any method of providing a disclosed composition, compounded composition, antimicrobial agent, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intra-aural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed composition, compounded composition, or antimicrobial agent can be administered pharmaceutically; that is, administered to treat an existing disease or condition. In further various aspects, a disclosed composition, compounded composition, or antimicrobial agent can be administered prophylactically; that is, administered for prevention of a disease or condition. In an aspect, the skilled person can determine an efficacious dose, an efficacious schedule, and an efficacious route of administration for a disclosed composition, compounded composition, or antimicrobial agent so as to treat a subject or inhibit or prevent an inflammatory reaction. In an aspect, the skilled person can also alter, change, or modify an aspect of an administering step so as to improve efficacy of a disclosed composition, compounded composition, or antimicrobial agent. In an aspect, administering means contacting at least a portion of one foot or both feet of a subject with agitated water comprising a disclosed composition, compounded composition, or antimicrobial agent in a footbath.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a lists of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

What is claimed is:

1. A method of treating a bacterial infection of a subject, the method comprising:
topically administering a topical composition to the subject comprising contacting a bacterial infected nail of the subject to be treated with the topical composition, wherein the topical composition has a solution, suspension, ointment, cream, gel, or lotion format and comprises dibasic calcium phosphate, hypromellose, lactose monohydrate, magnesium stearate, microcrystalline cellulose, polyethylene glycol, pregelatinized starch, titanium dioxide, triacetin, and an antimicrobial agent within a carrier, the antimicrobial agent comprising cefixime in an amount between approximately 200 mg and approximately 400 mg, wherein the carrier comprises an aqueous sodium chloride solution and the topical composition has a solution format, wherein administering the topical composition comprises contacting infected nail with the solution, and wherein the antimicrobial agent consists of the cefixime and nitrofurantoin.

2. The method of claim 1, wherein the topical composition is topically administered once or twice daily.

3. The method of claim 2, wherein the topical composition is topically administered twice daily and the topical composition comprises approximately 400 mg cefixime in each topical administration.

4. The method of claim 1, wherein the topical composition further includes carboxymethylcellulose sodium, anhydrous citric acid, glycerin, magnesium aluminum silicate, methylparaben, flavoring, propylparaben, purified water, saccharin sodium, sodium citrate, and sorbitol.

5. A method of treating a bacterial infection of a subject, the method comprising:

topically administering a topical composition to the subject comprising contacting a bacterial infected nail of the subject to be treated with the topical composition, wherein the topical composition has a solution, suspension, ointment, cream, gel, or lotion format and comprises dibasic calcium phosphate, hypromellose, lactose monohydrate, magnesium stearate, microcrystalline cellulose, polyethylene glycol, pregelatinized starch, titanium dioxide, triacetin, and an antimicrobial agent within a carrier, the antimicrobial agent comprising cefixime in an amount between approximately 200 mg and approximately 400 mg, wherein the carrier comprises an ointment, cream, gel, or lotion and the topical composition has an ointment, cream, gel, or lotion format, wherein administering the topical composition comprises applying the ointment, cream, gel, or lotion onto the infected nail, and wherein the antimicrobial agent consists of the cefixime and nitrofurantoin.

6. The method of claim 5, wherein the topical composition is topically administered once or twice daily.

7. The method of claim 6, wherein the topical composition is topically administered twice daily and the topical composition comprises approximately 400 mg cefixime in each topical administration.

* * * * *